US009678076B2

(12) United States Patent
Chait et al.

(10) Patent No.: US 9,678,076 B2
(45) Date of Patent: Jun. 13, 2017

(54) METHODS AND DEVICES FOR DETERMINING A DISEASE STATE

(71) Applicant: Analiza, Inc., Bay Village, OH (US)

(72) Inventors: Arnon Chait, Bay Village, OH (US); Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 0 days.

(21) Appl. No.: 14/312,907

(22) Filed: Jun. 24, 2014

(65) Prior Publication Data

US 2015/0369807 A1    Dec. 24, 2015

(51) Int. Cl.
*G01N 33/574* (2006.01)
*G01N 33/68* (2006.01)

(52) U.S. Cl.
CPC ....... *G01N 33/57415* (2013.01); *G01N 33/68* (2013.01); *G01N 33/6893* (2013.01); *G01N 2333/765* (2013.01); *G01N 2800/085* (2013.01); *G01N 2800/56* (2013.01)

(58) Field of Classification Search
CPC ............. G01N 33/57415; G01N 33/68; G01N 2333/765; G01N 2800/085; G01N 2800/56
See application file for complete search history.

(56) References Cited

U.S. PATENT DOCUMENTS

| | | | |
|---|---|---|---|
| 5,008,204 A | 4/1991 | Stehling | |
| 5,241,072 A | 8/1993 | Colon et al. | |
| 5,340,474 A | 8/1994 | Kauvar | |
| 5,734,024 A | 3/1998 | Zaslavsky | |
| 5,769,074 A | 6/1998 | Barnhill et al. | |
| 5,818,231 A | 10/1998 | Smith | |
| 5,948,750 A | 9/1999 | Garsky et al. | |
| 6,136,960 A | 10/2000 | Chait et al. | |
| 6,454,950 B1* | 9/2002 | Tjerneld | C07K 1/20 210/638 |
| 6,642,009 B2* | 11/2003 | Hung | A61B 10/0041 435/6.14 |
| 7,011,955 B1 | 3/2006 | Stemmler et al. | |
| 7,247,498 B2 | 7/2007 | Godec et al. | |
| 7,968,350 B2 | 6/2011 | Chait et al. | |
| 8,099,242 B2 | 1/2012 | Chait et al. | |
| 2001/0016590 A1 | 8/2001 | Ahotupa et al. | |
| 2002/0145425 A1 | 10/2002 | Ebbels et al. | |
| 2003/0162224 A1 | 8/2003 | Chait et al. | |
| 2004/0229375 A1 | 11/2004 | Chait et al. | |
| 2004/0236603 A1 | 11/2004 | Heller et al. | |
| 2006/0240416 A1 | 10/2006 | Banerjee et al. | |
| 2006/0255257 A1 | 11/2006 | Belgovskiy et al. | |
| 2006/0269964 A1 | 11/2006 | Chait et al. | |
| 2007/0048786 A1* | 3/2007 | Chait | C07K 1/36 435/7.1 |
| 2007/0059783 A1* | 3/2007 | Packer | G01N 33/574 435/7.23 |
| 2007/0128618 A1 | 6/2007 | Chait et al. | |
| 2007/0198194 A1* | 8/2007 | Chait | G01N 33/6848 702/19 |
| 2008/0050831 A1 | 2/2008 | Chait et al. | |
| 2011/0143453 A1* | 6/2011 | Van Eyk | G01N 33/6848 436/501 |
| 2011/0166028 A1* | 7/2011 | Bergstrom | C12Q 1/6886 506/7 |

FOREIGN PATENT DOCUMENTS

| | | |
|---|---|---|
| WO | WO 99/10522 A1 | 3/1999 |
| WO | WO 00/10674 A1 | 3/2000 |
| WO | WO 01/55698 A1 | 8/2001 |
| WO | WO 03/016883 A1 | 2/2003 |
| WO | WO 03/042694 A2 | 5/2003 |
| WO | WO 2004/111655 A1 | 12/2004 |
| WO | WO 2005/008247 A2 | 1/2005 |
| WO | WO 2006/124100 A2 | 11/2006 |
| WO | WO 2007/027561 A2 | 3/2007 |
| WO | WO 2008/005043 A2 | 1/2008 |
| WO | WO 2014/025961 A1 | 2/2014 |

OTHER PUBLICATIONS

Lis et al., Is Serum Albumin an Independent Predictor of Survival in Patients with Breast Cancer, Journal of Parenteral and Enteral Nutrition, 27(1), 10-15, 2003.*
Lowenthal, Analysis of Albumin-Associated Peptides and Proteins from Ovarian Cancer Patients, Clinical Chemistry, 51:10, 1933-1945, 2005.*
International Search Report and Written Opinion for Application No. PCT/US2015/037148 mailed Dec. 23, 2015.
Invitation to Pay Additional Fees for Application No. PCT/US2015/037148 mailed Sep. 30, 2015.
Fujii et al., Serum Albumin and Prealbumin Do Not Predict Recurrence in Patients with Breast Cancer. Anticancer Research. Jul. 1, 2014. 34: 3775-80.
Gupta et al., Pretreatment serum albumin as a predictor of cancer survival: A systematic review of the epidemiological literature. Nutrition Journal. Dec. 22, 2010. 9:1-16.

(Continued)

*Primary Examiner* — Andrea S Grossman
(74) *Attorney, Agent, or Firm* — Wolf, Greenfield & Sacks, P.C.

(57) ABSTRACT

The present invention, in some embodiments thereof, relates to methods and devices for determining a disease state in a patient. In some embodiments, human serum albumin may be analyzed for associated molecules, wherein the associated molecules are related to a disease such as cancer. Certain aspects of the invention are generally directed to devices and methods for determining a disease state as a function of the three-dimensional structure of a blood protein, human serum albumin (HSA) or its complex with other ligands, e.g., due to binding to disease-specific ligands. HSA interacts with biomolecules associated with a disease presence, and liganded HSA may differentially partition between aqueous phases of a predetermined partitioning system, wherein the partitioning behavior differs between HSA from healthy individuals and HSA from people harboring the predetermined disease, such as breast cancer.

7 Claims, 8 Drawing Sheets

(56) References Cited

OTHER PUBLICATIONS

Lebreton et al., Application of aqueous two-phase partition to the production of homogeneous preparations of fluorescently labelled human serum albumin. Journal of Chromatography B. Jun. 23, 2000. 743(1-2): 263-9.

Nasim et al., Original Research: Potential Biomarkers in the Sera of Breast Cancer Patients from Bahawalpur, Pakistan. Biomarkers in Cancer. Dec. 1, 2012. 4: 19-34.

Albertsson et al., English Language Abstract of Separation processes in biotechnology. Bioprocess Technology, vol. 9, pp. 287-327, 1990.

Andrews et al., Affinity gel electrophoresis as a predictive technique in the fractionation of transgenic sheep milk proteins by affinity aqueous two-phase partitioning. Biotechnology Letters, vol. 22, pp. 1349-1353, 2000.

Arnoldi et al., Lipophilicity-Antifungal Activity Relationships for Some Isoflavonoid Phytoalexins. Journal of Agricultural and Food Chemistry, vol. 38, No. 3, 1990, pp. 834-838.

Atktinson et al., Trypsin and alpha-chymotrypsin partitioning in polyethylene glycol/maltodextrin aqueous two-phase systems. Food and Bioproducts Processing, 1994, 72 (C2):106-112.

Berggren et al., Substitutions of surface amino acid residues of cutinase probed by aqueous two-phase portioning. Biochimica et Biophysica Acta, vol. 1481, pp. 317-327, 2000.

Bevan et al., A High-Throughput Screening Method for the Determination of Aqueous Drug Solubility Using Laser Nephelometry in Microtiter Plates. Analytical Chemistry, Apr. 15, 2000, vol. 72, No. 8, pp. 1781-1787.

Bodnar et al., Exploiting the Complementary Nature of LC/MALDI/MS/MS and LC/ESI/MS/MS for Increased Proteome Coverage. J. Am. Soc. Mass. Spectrom 2003, 14, 971-979.

Chait, From Structure to Signature. 8.sup.th Annual SBS Conference & Exhibition, Sep. 22-26, 2002, Netherlands Congress Centre, The Hague, The Netherlands.

Chait, HTS Technology for Analysis of Structural Signatures of Biomolecules: Methodology and Applications. California Separation Science Society, WCBP 2002, 6.sup.th Symposium on the Interface of Regulatory and Analytical Sciences for Biotechnology Health Products, Jan. 27-30, 2002.

Durand et al., Protein Glycosylation and Diseases: Blood and Urinary Oligosaccharides as Markers for Diagnosis and Therapeutic Monitoring. Clinical Chemistry 46:6, pp. 795-805 (2000).

Everberg et al., Protein pre-fractionation in detergent-polymer aqueous two-phase systems for facilitated proteomic studies of membrane proteins. J Chromatogr A (2004) 1029:113-124.

Guiliano, English Language Abstract of Aqueous two-phase protein partitioning using textile dyes as affinity ligands. Analytical Biochemistry, vol. 197, No. 2, pp. 333-339, 1991.

Gulyaeva et al., Relative hydrophobicity of organic compounds measured by partitioning in aqueous two-phase systems. Journal of Chromatography B, vol. 743, pp. 187-194, 2000.

Guzzetta Reverse Phase HPLC Basics for LC/MA. An Ion Source Tutorial, published Jul. 22, 2001.

Harboe, et al., Generation of Antibodies to the Signal Peptide of the MPT83 Lipoprotein of Mycobacterium Tuberculosis. Scandinavian Journal of Immunology, vol. 55, No. 1, Jan. 2002, pp. 82-87.

Kohwi et al., Amphipathic Lipid-Bound Protein Antigents in Mouse Bladder Carcinomas Detected by a Monoclonal Antibody. Biochemestry, vol. 23, No. 25, 1984 pp. 5945-5950.

Kuboi et al., Evaluation of surface hydrophobicities of proteins using hydrophobic interaction with non-ionic surfactants in aqueous two-phase partitioning systems. Kagaku Kogaku Ronbunshu, vol. 19, No. 3, pp. 446-454, 1993.

Mueller et al., Real and Pseudo Oxygen Gradients in Ca-alginate Beads Monitored During Polarographic PO-2-measurements using Pt-needle microelectrodes. Biotechnology and Bioengineering, vol. 44, No. 5, 1994, pp. 617-625.

Peracaula et al., Altered glycosylation pattern allows the distinction between prostate-specific antigen (PSA) from normal and tumor origins. Glycobiology, vol. 13, No. 6, pp. 457-470, 2003.

Platt et al., QSAR in grossly underdetermined systems: Opportunities and issues. IBM Journal of Research and Development, vol. 45, 2001 (web page).

[No Author Listed], Program listing of the Society of Biomoecular Screening 2002, Session 2A Technical Program for the 8th Annual SBS Conference & Exhibition, Sep. 22-26, 2002, Netherlands Congress Centre, The Hague, The Netherlands.

[No Author Listed], Program listing of the Well-Characterized Biologics Conference 2002, California Separation Science Society, WCBP 2002, 6th Symposium on the Interface of Regulatory and Analytical Sciences for Biotechnology Health Products, Jan. 27-30, 2002.

[No Author Listed], QSAR Introduction. http://www.chem.swin.edu.au/modules/mod4/qsarrefs.htm [last accessed Jul. 2, 2007].

Richon et al., An Introduction to QSAR Methodology. Oct. 1997.

Sakurai et al., English Language Abstract of Ligand and nuclear factor-dependent change in hydrophobicity of thyroid hormone [beta] 1 receptor. Thyroid, vol. 8, No. 4, pp. 343-352, 1998.

Schena et al., Parallel human genome analysis: Microarray-based expression monitoring of 1000 genes. Proc. Natl. Acad. Sci. vol. 93, pp. 10614-10619, Oct. 1996.

Singh et al., Gene expression correlates of clinical prostate cancer behavior. Cancer Cell: Mar. 2002, vol. 1, pp. 203-209.

Sniegoski, An Examination of the Concentration of Organic Components Water-Extracted From Petroleum Products. Water Research, vol. 9, pp. 421-423 (1975).

Stovsky et al., PSA/SIA: A New Highly Sensitive and Specific Structure-Based Assay for Prostate Cancer. Poster, AUA NC 82nd Annual Meeting, Chicago, IL, Sep. 24-27, 2008.

Stovsky et al., Prostate-specific antigen/solvent interaction analysis: a preliminary evaluation of a new assay concept for detecting prostate cancer using urinary samples. Urology. Sep. 2011;78(3):601-5. doi: 10.1016/j.urology.2011.03.071. Epub Jul. 23, 2011.

Takano et al., Measuring the Solubility of Liquid Organic Compounds in Water. Journal of the Chemical Society of Japan, 1985, (11), pp. 2116-2119.

Takano et al., Solubility Measurement of Liquid Organic Compounds in Water, Nippon Kagaku Kaishi, 1985, vol. 11, pp. 2116-2119. Chemical Abstract No. 105:60254. CAS Online, Columbus, Ohio.

Yan, Detection by ozone-induced chemiluminescence in chromatography. Journal of Chromatography, 842 (1999), pp. 267-308.

Zaslavsky, Aqueous Two-Phase Partitioning (book), Marcel Dekker, NY, 1995.

Zaslavsky, Characteristics of Protein-Aqueous Medium Interactions Measured by Partition in Aqueous Ficoll-Dextran Biphasic System. J. Chromatogr., 1983, 260:329-336.

Zaslaysky et al., A New Method for Analysis of Components in a Mixture without Preseparation: Evaluation of the Concentration Ratio and Protein-Protein Interaction. Analytical Biochemistry, vol. 296, pp. 262-269, 2001.

* cited by examiner

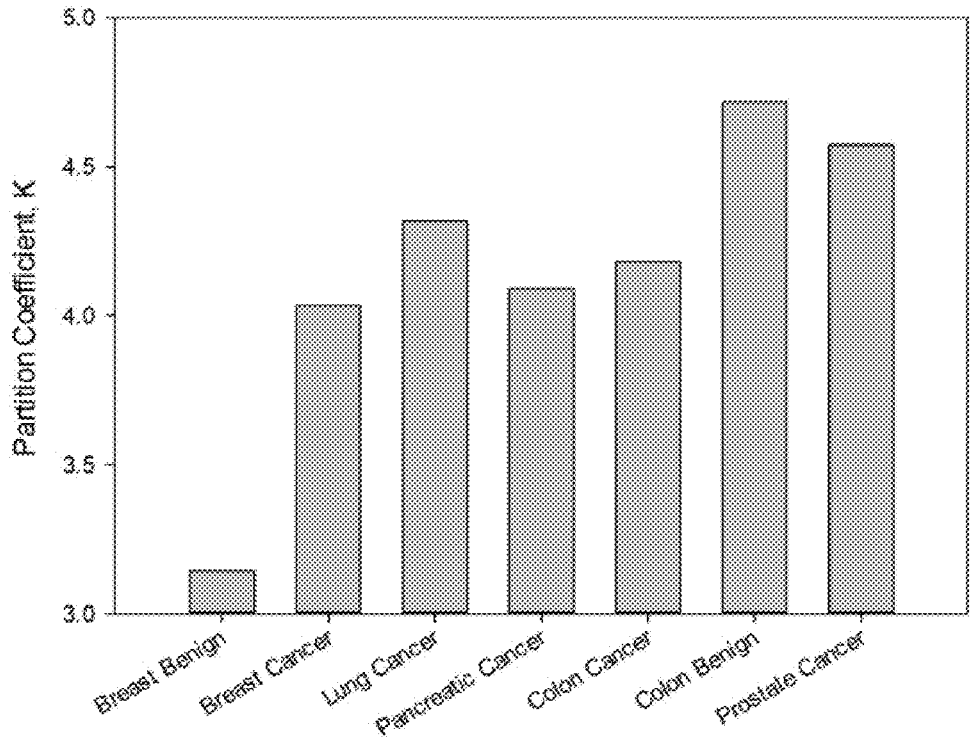

FIG. 8

MKWVTFISLL FLFSSAYSRG VFRRDAHKSE VAHRFKDLGE ENFKALVLIA FAQYLQQCPF EDHVKLVNEV
TEFAKTCVAD ESAENCDKSL HTLFGDKLCT VATLRETYGE MADCCAKQEP ERNECFLQHK DDNPNLPRLV
RPEVDVMCTA FHDNEETFLK KYLYEIARRH PYFYAPELLF FAKRYKAAFT ECCQAADKAA CLLPKLDELR
DEGKASSAKQ RLKCASLQKF GERAFKAWAV ARLSQRFPKA EFAEVSKLVT DLTKVHTECC HGDLLECADD
RADLAKYICE NQDSISSKLK ECCEKPLLEK SHCIAEVEND EMPADLPSLA ADFVESKDVC KNYAEAKDVF
LGMFLYEYAR RHPDYSVVLL LRLAKTYETT LEKCCAAADP HECYAKVFDE FKPLVEEPQN LIKQNCELFE
QLGEYKFQNA LLVRYTKKVP QVSTPTLVEV SRNLGKVGSK CCKHPEAKRM PCAEDYLSVV LNQLCVLHEK
TPVSDRVTKC CTESLVNRRP CFSALEVDET YVPKEFNAET FTFHADICTL SEKERQIKKQ TALVELVKHK
PKATKEQLKA VMDDFAAFVE KCCKADDKET CFAEEGKKLV AASQAALGL (SEQ ID NO: 1)

FIG. 9

SEQUENCE LISTING

```
<160> NUMBER OF SEQ ID NOS: 1

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60
```

-continued

```
Lys Leu Val Asn Glu Val Thr Glu Phe Ala Lys Thr Cys Val Ala Asp
 65              70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480
```

-continued

```
Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```

METHODS AND DEVICES FOR DETERMINING A DISEASE STATE

FIELD

The present invention, in some embodiments thereof, relates to methods and devices for determining a disease state in a patient. In some embodiments, human serum albumin may be analyzed for associated molecules, wherein the associated molecules are related to a disease such as cancer.

BACKGROUND

There are two considerations generally relating to cancer: it is the number one killer in the United States (when taken as an aggregate of the multiple forms of the disease) and the earlier the detection the greater the likelihood for a positive outcome. Cancers are often discovered only when they are large enough to be seen with an imaging device or when they have spread so much that they have severely affected the health of the ill patient.

Cancer diagnostics suffer from several major challenges. Some tests, notably PSA (prostate-specific antigen) tests for prostate cancer, are often inaccurate harbingers of the disease's presence. Additionally, some tests require unpleasant surgery or the like to obtain biopsies. Other tests, notably the BRAC series of genetic tests for breast cancer, are prohibitively expensive. An ideal cancer diagnostic would require nothing more than a blood sample and would give highly accurate and reliable results, even for "small" cancers that have not yet reached a size easily visible on X-ray, CAT, and MRI machines.

The prior art generally describes methods for determining a disease state directly from the presence of a predetermined biomolecule produced as a result of said disease state. Improvements in determining disease states, including but not limited to cancers, are thus needed.

SUMMARY

The present invention, in some embodiments thereof, relates to methods and devices for determining a disease state in a patient. In some embodiments, human serum albumin may be analyzed for associated molecules, wherein the associated molecules are related to a disease such as cancer. The subject matter of the present invention involves, in some cases, interrelated products, alternative solutions to a particular problem, and/or a plurality of different uses of one or more systems and/or articles.

It is therefore a purpose of the present invention, in some embodiments, to describe methods and devices for determining a disease state as a function of the interaction behavior of a blood component, such as human serum albumin (HSA). In some embodiments of the invention, the interaction of HSA with at least one biomolecule related to a disease state may cause HSA to partition differently in a biphasic aqueous system, as compared to HSA from blood of a healthy individual.

The invention includes, in certain embodiments, a method for diagnosing breast cancer, other cancers, or other disease states. In one embodiment, the method comprises the following: collecting blood from a patient; separating serum or plasma from the blood; partitioning the serum or plasma in at least one aqueous two-phase partitioning system; assaying aqueous phases of the at least one two phase partitioning system for human serum albumin (HSA) using at least one assay specific for the albumin; calculating or determining the partition coefficient K of albumin for each aqueous phase of the two phase partitioning system; and, determining presence or risk level of breast cancer or other cancer in the patient by comparing numerical values of calculated partition coefficients with reference values previously determined for HSA in serum or plasma taken from individuals with and without breast cancer or other cancers.

In one aspect of the method, the assaying is performed with an HSA-specific immuno-based assay.

In another aspect of the method, the assaying is performed with an assay that is specific for a biomolecule that is associated with HSA.

In another aspect of the method, the two-phase partitioning system is adapted to differentially partition albumin when cancer is present or absent in the patient.

In another aspect of the method, the method is applied in conjunction with a mammogram, genetic, or other cancer test.

In another aspect of the method, the method is applied as a part of a mathematical or statistical algorithm, in conjunction with information obtained from a mammogram, genetic, or other cancer test.

In another aspect of the method, the individuals without cancer include individuals with benign tumors.

In another aspect of the method, the diagnosing is used to screen, diagnose, classify according to phenotype/genotype, aid in therapeutic course of action, monitor progression, or detect recurrence of cancer.

In another aspect of the method, the diagnosis is performed by comparing the value of the partition coefficient, K, to its prior value or values at prior time or times of the same individual.

In another aspect of the method, the numerical value of the partition coefficient is used to select a therapeutic drug.

In another aspect of the method, the partitioning involves vortexing and centrifugation of the two-phase partitioning system with human serum albumin present.

In another aspect of the method, there is an additional step of removing at least one biomolecule from the human serum albumin.

In another aspect of the method, the at least one peptide is characterized for use as a biomarker for cancer presence or risk.

In another aspect of the method, the reference values are determined from blood samples taken from individuals with and free of cancer.

The invention also provides, in some embodiments, a device for the detection of breast cancer or other cancers or disease states. In some cases, the device includes: a unit for collecting blood from a patient and separating serum or plasma from the blood; at least one aqueous two-phase partitioning system; a unit for partitioning a portion of the serum or plasma in the two phase partitioning system; an assay for determining the presence of human serum albumin in aqueous phases of the two phase partitioning system; a computing element adapted to determine a coefficient K, wherein K represents the distribution of human serum albumin in the aqueous portions of the two-phase partitioning system; and, a determination element adapted to compare the coefficient K with known values of K for blood samples of healthy individuals and individuals with breast cancer or other cancers.

In one aspect of the device, the assay is realized as an HSA-specific immuno-based assay.

In another aspect of the device, there is additionally a microfluidics device.

In another aspect of the device, the two-phase partitioning system is adapted to differentially partition albumin when cancer is present or absent in the patient.

In another aspect of the device, the computing element and the determination element are realized as a single element associated with a computing device.

In another aspect of the device, the computing device is realized as one of the following: mainframe computer, laptop computer, tablet computer, mobile computing device, and tabletop computer.

In another aspect of the device, the unit for partitioning includes a centrifuge component.

In another aspect of the device, the microfluidics device does not include vortexing or centrifugation in the unit for partitioning.

The invention additionally includes, in some embodiments, a method for diagnosing a disease in a patient. The method, in some cases, comprises the following: collecting blood from the patient; separating serum or plasma from the blood; partitioning the serum or plasma in at least one aqueous two-phase partitioning system, wherein the two-phase partitioning system is adapted to differentially partition albumin when the disease is present or absent in the patient; assaying aqueous phases of the at least one two phase partitioning system for human serum albumin (HSA) using specific assay for the albumin; calculating or determining partition coefficient K of albumin for each aqueous phases; and, determining presence of the disease in the patient by comparing numerical values of calculated partition coefficients with reference values previously determined for albumin in serum or plasma taken from individuals with and without the disease.

In one aspect of the method, the disease is cancer.

In another aspect of the method, the cancer is selected from the following: throat cancer, stomach cancer, pancreatic cancer, brain cancer, lung cancer, cervical cancer, prostate cancer, breast cancer, testicular cancer, ovarian cancer, oral cancer, throat cancer, esophagus cancer, and intestinal cancer and intestinal cancer.

In another aspect of the method, the disease is realized as a plurality of diseases.

In another aspect of the method, the disease is hereditary.

In another aspect of the method, the partition coefficients obtained from a plurality of aqueous two-phase systems are combined using mathematical techniques into a numerical signature.

In another aspect of the method, the numerical signature is compared with numerical signatures obtained from reference values and is used for diagnosis.

Still another aspect of the present invention is generally directed to a method for diagnosing breast cancer. In one set of embodiments, the method comprises acts of collecting blood from a patient, separating serum or plasma from said blood, partitioning said serum or plasma in at least one aqueous two-phase partitioning system, assaying aqueous phases of said at least one two phase partitioning system for human serum albumin (HSA) using at least one assay specific for said albumin, calculating partition coefficient K of albumin for each aqueous phase of said two phase partitioning system, and determining presence, lack of, or risk level of breast cancer in said patient by comparing numerical values of calculated partition coefficients with reference values previously determined for HSA in serum or plasma taken from individuals with and without breast cancer.

In another set of embodiments, the method includes acts of collecting blood from a patient, separating serum or plasma from said blood, partitioning said serum or plasma in at least one aqueous two-phase partitioning system, assaying aqueous phases of said at least one two phase partitioning system for human serum albumin (HSA) using at least one assay specific for said albumin, calculating partition coefficient K of albumin for each aqueous phase of said two phase partitioning system, and determining presence, lack of, or risk level of cancer in said patient by comparing numerical values of calculated partition coefficients with reference values previously determined for HSA in serum or plasma taken from individuals with and without cancer.

The method, in another aspect, is generally directed to a method for diagnosing a disease in a patient. In one set of embodiments, the method includes acts of collecting blood from said patient, separating serum or plasma from said blood, partitioning said serum or plasma in at least one aqueous two-phase partitioning system, wherein said two-phase partitioning system is adapted to differentially partition albumin when said disease is present or absent in said patient, assaying aqueous phases of said at least one two phase partitioning system for human serum albumin (HSA) using specific assay for said albumin, calculating partition coefficient K of albumin for each aqueous phases, and determining presence of said disease in said patient by comparing numerical values of calculated partition coefficients with reference values previously determined for albumin in serum or plasma taken from individuals with and without said disease.

In yet another aspect, the method is generally directed to acts of partitioning a sample arising from a subject in an aqueous two-phase partitioning system, and determining the distribution of human serum albumin within the phases of the two-phase partitioning system.

Still another aspect of the present invention is generally directed to a device. According to one set of embodiments, the device is a device for the detection of breast cancer. In one set of embodiments, the device comprises a unit for collecting blood from a patient and separating serum or plasma from said blood, at least one aqueous two-phase partitioning system in fluid communication with the unit for collecting blood, a unit for partitioning a portion of said serum or plasma in said two phase partitioning system in fluid communication with the partitioning system, an assay for determining the presence of human serum albumin in aqueous phases of said two phase partitioning system, a computing element adapted to determine a coefficient K, wherein K represents the distribution of human serum albumin in the aqueous portions of said two-phase partitioning system, and a determination element adapted to compare said coefficient K with known values of K for blood samples of healthy individuals and individuals with breast cancer.

In another set of embodiments, the device is a device for the detection of cancer. In certain embodiments, the device comprises a unit for collecting blood from a patient and separating serum or plasma from said blood, at least one aqueous two-phase partitioning system in fluid communication with the unit for collecting blood, a unit for partitioning a portion of said serum or plasma in said two phase partitioning system in fluid communication with the partitioning system, an assay for determining the presence of human serum albumin in aqueous phases of said two phase partitioning system, a computing element adapted to determine a coefficient K, wherein K represents the distribution of human serum albumin in the aqueous portions of said two-phase partitioning system, and a determination element adapted to compare said coefficient K with known values of K for blood samples of healthy individuals and individuals with cancer.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 8 shows the differences between the value of the partition coefficient of HSA for breast cancer samples in Table 4, and non-cancerous samples, including benign breast cancer and other cancers and benign conditions, in another embodiment; and FIG. 9 shows human serum albumin (SEQ ID NO: 1).

DETAILED DESCRIPTION

The present invention, in some embodiments thereof, relates to methods and devices for determining a disease state in a patient. In some embodiments, human serum albumin may be analyzed for associated molecules, wherein the associated molecules are related to a disease such as cancer. Certain aspects of the invention are generally directed to devices and methods for determining a disease state as a function of the three-dimensional structure of a blood protein, human serum albumin (HSA) or its complex with other ligands, e.g., due to binding to disease-specific ligands. HSA interacts with biomolecules associated with a disease presence, and liganded HSA may differentially partition between aqueous phases of a predetermined partitioning system, wherein the partitioning behavior differs between HSA from healthy individuals and HSA from people harboring the predetermined disease, such as breast cancer.

For instance, in some embodiments, the present invention is generally related to methods and devices for detecting the presence or risk of acquiring a disease state as related to differential solubility behavior of human serum albumin (HSA) as it is associated with ligands related to said disease state. Aqueous partitioning systems are employed wherein the partitioning of liganded HSA is differentiated between healthy and disease states.

HSA, being the most abundant blood protein and the major carrier of both small and large compounds, is typically not considered as a useful source of information for assessment of a physiological state or condition of a subject. Indeed, HSA is usually first removed from serum or plasma before analysis, since the concentration of HSA is much greater than signaling or other proteins of interest. In some cases, excess HSA may be present in a blood sample, such as serum or plasma, by up to 11 orders of magnitude over other proteins of interest, thus significantly potentially masking other proteins during analysis. Accordingly, HSA is typically seen as undesirable for biomarker discover or analysis.

Furthermore, as HSA is present in the blood in high concentrations compared to other proteins, HSA often interacts with almost everything in the blood or the body, e.g., to a degree that significantly masks other proteins of interest. Accordingly, due to its ubiquity and its ability to interact with other components in the blood, HSA has not generally been considered to be useful in the analysis of any specific diseases or conditions, such as cancer. Instead, as noted above, HSA is usually ignored or filtered out of the blood. Accordingly, it is surprising that HSA would be of any utility or interest in diagnosing specific medical diseases or conditions, such as breast cancer or other cancers or diseases such as those discussed in greater detail below.

Figure 1:
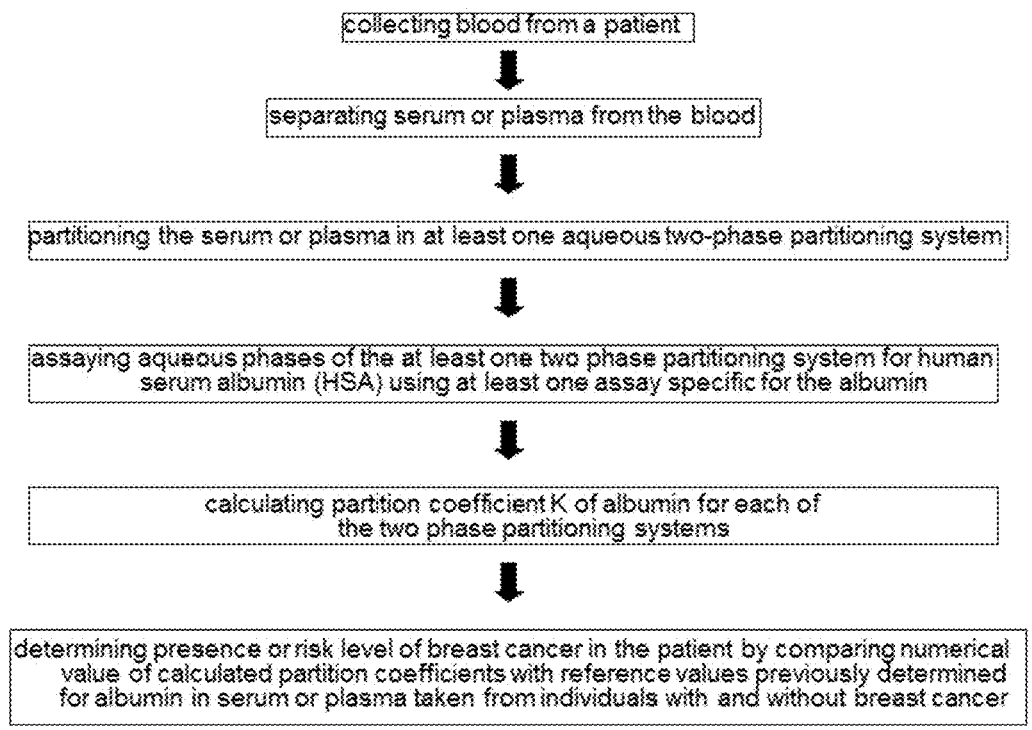
FIG. 1 shows a flowchart related to a method of one embodiment of the present invention.

For purposes of better understanding some embodiments of the present invention, as illustrated in FIGS. 1-8 of the drawings, reference is first made to FIG. 1. FIG. 1 shows a flowchart of a method of one embodiment of the invention. The method steps include, in this example, the following: collecting blood from a patient; separating serum or plasma from the blood; optionally performing additional fractionation and/or sample preparation steps to further separate certain species; partitioning the serum or plasma in at least one aqueous two-phase partitioning system; assaying aqueous phases of the at least one two phase partitioning system for human serum albumin (HSA) using at least one assay specific for the albumin; calculating or determining partition coefficient K of albumin for each aqueous phase of the two phase partitioning system; and, determining presence or risk level of breast cancer in the patient by comparing numerical values of calculated partition coefficients with reference values previously determined for HSA in serum or plasma taken from individuals with and without breast cancer. This allows for detection of or determination of risk for breast cancers, or other cancers, via a traditional blood sample.

In some cases, blood is collected and the serum or plasma is isolated and analyzed.

Human serum albumin is the most abundant protein in the serum. HSA has a tendency to interact with or bind proteins, peptides or other biological ligands, serving as carrier protein for many small and large molecules. These biomolecules may come from myriad cellular sources and their specific functions may be unknown. However, since HSA half-life in circulation is over 20 days, its role as carrier protein may allow circulating disease-associated peptides and other molecules to accumulate in time. Thus, even small amounts of a disease-associated biomolecules, e.g., from a small tumor, which continuously enter the circulation, could be amplified in time by binding to HSA, thus avoiding clearance mechanisms. Accordingly, in some embodiments, a blood sample (or other suitable fluid sample) containing HSA is collected from a patient. Any suitable technique known to those of ordinary skill in the art may be used to collect blood or other suitable fluids.

In some embodiments, HSA in the blood may be partitioned between aqueous phases in a predetermined biphasic (or higher, i.e., multiphasic) liquid system. The HSA enters one or more of the phases, but in general not at equal levels, e.g., due to differences in the aqueous solvent characteristics in the two phases. Without wishing to be bound by any theory, it is believed that the specific amount of HSA entering a phase may be further related to associated ligands on the HSA. In some cases, the specific ligands associated with the HSA may not even be known, identified, or understood; however, differences in HSA can still be readily determined, e.g., causing different partitioning between the aqueous phases. For instance, the HSA dissolved in each phase may vary between healthy (including benign) patients and those with breast cancer. In addition, it should be understood that although breast cancer is used here, this is by way of example only, and other cancers may also be determined, not just breast cancer. The subject may be male or female, as both sexes can be afflicted by a variety of cancers, including but not limited to breast cancers. The subject is typically human, although non-human animals may be studied in certain embodiments (e.g., using the appropriate species instead of human serum albumin, e.g., bovine serum albumin in the case of cow).

Thus, in some embodiments, the aqueous-based liquids used in the partitioning system are pre-selected to provide this differentiation of HSA behavior as a function of presence or absence of cancers (or the risk of cancers), such as breast cancers, in a patient. In some cases, the specific form of cancer may not necessarily be readily identified, e.g., a cancer may nevertheless cause changes in HAS partitioning, even if the cancer itself is not identified.

Once the HSA has been partitioned, in steps that may involve, e.g., vortexting, mixing, centrifugation, or other manipulations, the HSA in each phase may be assayed using techniques known to those of ordinary skill in the art. Examples include, but are not limited to, immuno-specific assays like ELISA. Such assays may be directed towards a ligand or a plurality of ligands associated with the HSA, if it is known, although this is not always required. With quantification of HSA or its associated ligands in both phases after partitioning, one may determine a ratio of the amount of HSA (or ligands) in each phase. This ratio, K, may vary significantly in some cases between HSA taken from healthy patients and those with cancers or high risk for cancers, e.g., with pre-cancerous growths. For instance, patients with an active breast cancer or those with a high risk for the disease may be determined in various embodiments. In some cases, K may be compared to data previously collected for known healthy and known ill patients, or compared with data collected earlier from the same patient presumably in a healthy state. The K value may be determined as falling within values for healthy patients or within values for those known to have breast or other cancers, or a high risk factor for such cancers, etc. Since the individual disease biology may differ for each individual, conventional statistical techniques known to those of ordinary skill in the art used in the study of diagnostics, such as Receiver-Operating Characteristics, may be used to define a cut-off point for K, depending on the desired levels of sensitivity and specificity.

The ligands associated with HSA which allow for the differentiation may never be known, in some cases. Moreover, since cancer is a heterogeneous disease on the molecular level, such methods, which focuses on differential solubility of the HSA carrier protein that potentially binds a myriad of disease-associated molecules, may be advantageous in comparison with the conventional approach of isolating a single "silver bullet" biomarker. For instance, the ligands binding to HSA may, in reality, be composed of a family of different ligands or biomarkers, and their aggregate effect on HSA may be determined, even if the effect of any single biomarker is not completely determined. In some embodiments, one may isolate said ligands for the purpose of assigning them as biomarkers for certain cancers, such as breast cancer. Methods for removing biomolecules from HSA and analyzing said biomolecules are those traditionally used in protein chemistry work, and include chromatography, mass spectrometry, etc. Since one does not have to initially identify and define biomarkers in this embodiment, a great deal of effort may be saved instead by analyzing changes in HSA partitioning behavior as a function of the presence or absence of cancer, or the risk of cancer, according to certain embodiment of the invention.

The approximate sequence of human serum albumin (SEQ ID NO: 1) is shown in FIG. 9. The italicized first 24 amino acids are signal and propeptide portions not observed in the transcribed, translated, and transported protein but present in the gene. There are 609 amino acids in this sequence with only 585 amino acids in the final product observed in the blood.

Figure 2:
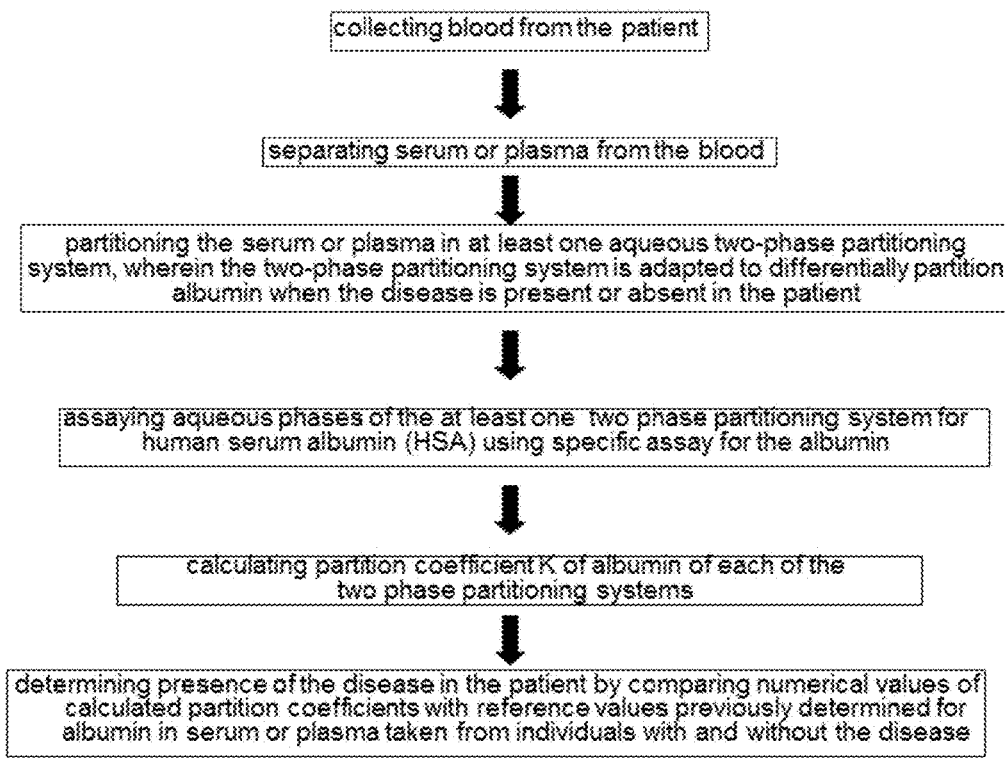
FIG. 2 shows a flowchart of method associated with another embodiment of the invention.

Attention is now turned to FIG. 2, which shows a flowchart for a method associated with another embodiment. The method steps include the following: collecting blood from a patient; separating serum or plasma from the blood; partitioning the serum or plasma in at least one aqueous two-phase partitioning system, wherein the two-phase partitioning system is adapted to differentially partition albumin when the disease is present or absent in the patient; assaying aqueous phases of the at least one two phase partitioning system for human serum albumin (HSA) using specific assay for the albumin; calculating or determining partition coefficient K of albumin for each aqueous phases; and, determining presence of the disease in the patient by comparing numerical values of calculated partition coefficients with reference values previously determined for albumin in serum or plasma taken from the same individuals or from individuals with and without the disease. This allows for detection of or determination of a predetermined disease state via a traditional blood sample. Blood is collected and the serum or plasma is analyzed. In some cases, HSA is partitioned between aqueous phases in a predetermined biphasic (or higher) liquid system. The HSA enters both phases, but in general not at equal levels due to differences in the aqueous solvent characteristics in the two phases, e.g., as discussed above. The specific amount entering a phase may be further being related to HSA having at least one associated ligand, wherein the ligand has some relationship to the presence of the disease state in the patient. Additionally, the HSA dissolved in each phase may vary between healthy (defined as those lacking the specific disease in question) patients and those with the predetermined disease.

The liquids used in the partitioning system may be pre-selected in some cases to provide this differentiation of HSA behavior as a function of presence or absences of said disease in a patient, or to determining the risk of the disease in the patient. Once the HSA has been partitioned, in steps that may involve vortexing, centrifugation, microfluidic transfer or other manipulations, the HSA in each phase may be assayed using techniques known to those of ordinary skill in the art. Examples include, but are not limited to, immuno-specific assays like ELISA. With identification of HSA and its quantification, one may determine a ratio of HSA in each phase. This ratio, K, may in some cases vary significantly between HSA taken from healthy patients and those with the predetermined disease. K is thus compared to data previously collected for known healthy and known ill patients. The K value will either fall within values for healthy patients or within values for those known to have the disease in question. Diseases that can be determined include, but are not limited to cancers, hereditary diseases, bacterial infections, viral infections, and sepsis. In some cases, any disease which causes any alteration in ligands that associate with HAS in the blood can be determined, in accordance with various embodiments of the invention.

Preparation of partitioning systems for various aspects of the invention, including those described above, may, in some cases, involves large-scale robotic screening of liquid samples to determine which liquids provide analytical differentiation of HSA from healthy samples and those who have the predetermined disease associated with the assay under development. Once a solvent system, comprising two, three, or more immiscible liquid layers, is defined, HSA from people of unknown health conditions (e.g., having a disease such as cancer, or other diseases described herein) may be partitioned, assayed, and analyzed. K values determined may be compared to known K values for healthy people and K values for those known to be ill or at risk for the predetermined disease, or compared with K values of the same individual at earlier time (presumably at a healthy state).

One aspect of the present invention is generally directed to HSA. HSA is an abundant blood protein. Without wishing to be bound by any theory, determining HSA in the blood, e.g., through partitioning as discussed herein, may be useful for determining disease states in an individual, e.g., through comparison with other healthy and/or diseased individuals. In and of itself, HSA does not give much information on disease states in the blood or in other organs of the body. Yet, it is the nature of HSA to bind peptides, proteins and other biomolecules. The ensuing result of the binding behavior would appear to be different between healthy and ill individuals as a function of potential ligands available for HSA interaction: HSA isolated from the blood of ill people appears to have different ligands than does HSA isolated from healthy people. One advantage of the instant invention is that one does not have to identify, isolate, or otherwise define a biomarker for a given disease or illness condition. Indeed, it may be exceedingly difficult or even impossible to define a disease condition based on a unique biomarker for complex, heterogeneous diseases such as cancer. Rather, one may use HSA's proclivity for binding proteins and the ability to differentially dissolve HSA in a plurality of solvents, e.g., due to its modified three or higher dimensional structure when bound up with various ligands. Dissolution of HSA may be different not only between solvents, but also different as a function of HSA liganded with proteins and the like from a healthy person and HSA liganded with proteins and the like from a patient harboring disease. Yet another advantage of focusing on HSA and its bound biomolecules is related to its long life in circulation—over 20 days— which may in some cases serve to amplify the effect of even small amounts of disease-associated biomolecules that continuously enter the circulation over time.

Figure 3:
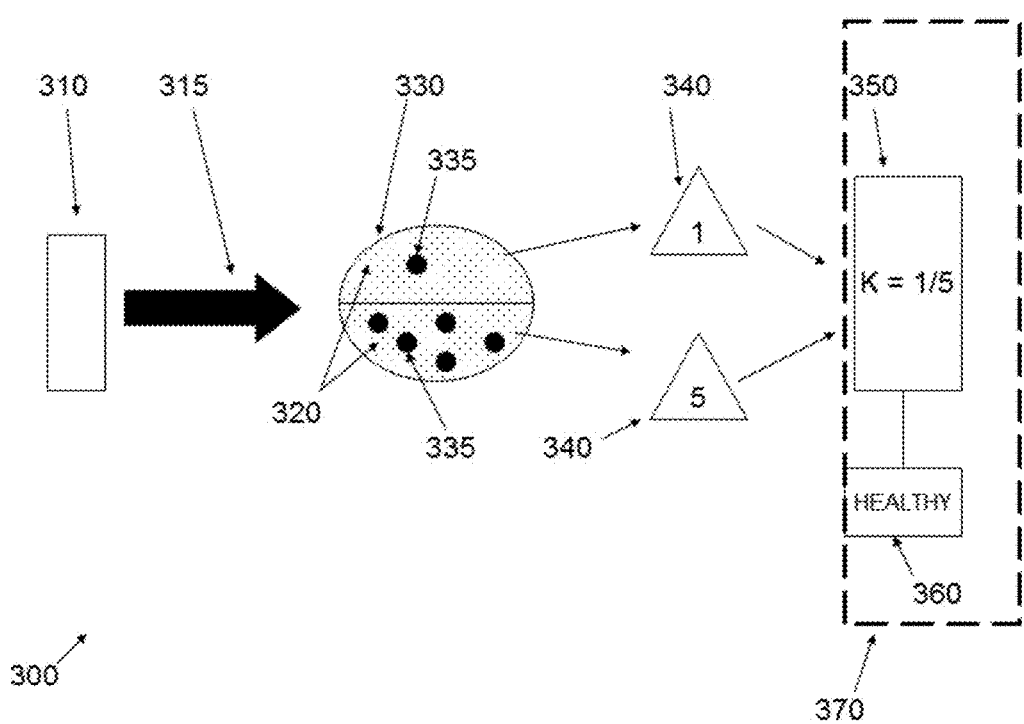
FIG. 3 shows a schematic view of yet another embodiment of the invention.

Attention is turned to FIG. 3 which is directed to an example of a device. The components of a device associated with the cancer detection system 300 include: a unit for collecting blood 310 from a patient and separating 315 serum or plasma from the blood; at least one aqueous two-phase partitioning system 320; a unit for partitioning 330 a portion of the serum or plasma in the two phase partitioning system; an assay 340 for determining the presence of human serum albumin 335 in aqueous phases of the two phase partitioning system; a computing element 350 adapted to determine a coefficient K, wherein K represents the distribution of human serum albumin 335 in the aqueous portions of the two-phase partitioning system; and, a determination element 360 adapted to compare the coefficient K with known values of K for blood samples of healthy individuals and individuals with cancer. The unit for collecting blood may, for example, include a needle or syringe. In some cases, one or more of these units may be contained within a single device.

It should be understood that all of the elements described in this embodiment may be included in a single unit or a small number of modular components; the elements are shown individually so as to aid in the understanding of the present invention. For example, computing element 350 and determination element 360 may generally be associated with a computing device 370 that may including a controller element (not shown) that directs various tasks from the receipt of blood to producing a final determination of the presence or absence of cancer, or the risk of cancer in some cases. Computing device 370 may be realized as any relevant device and includes but is not limited to computers, hand-held computers, tablet computers, cellular phones, laptop computers, and tabletop computers, or other computing devices known to those of ordinary skill in the art.

Figure 4:
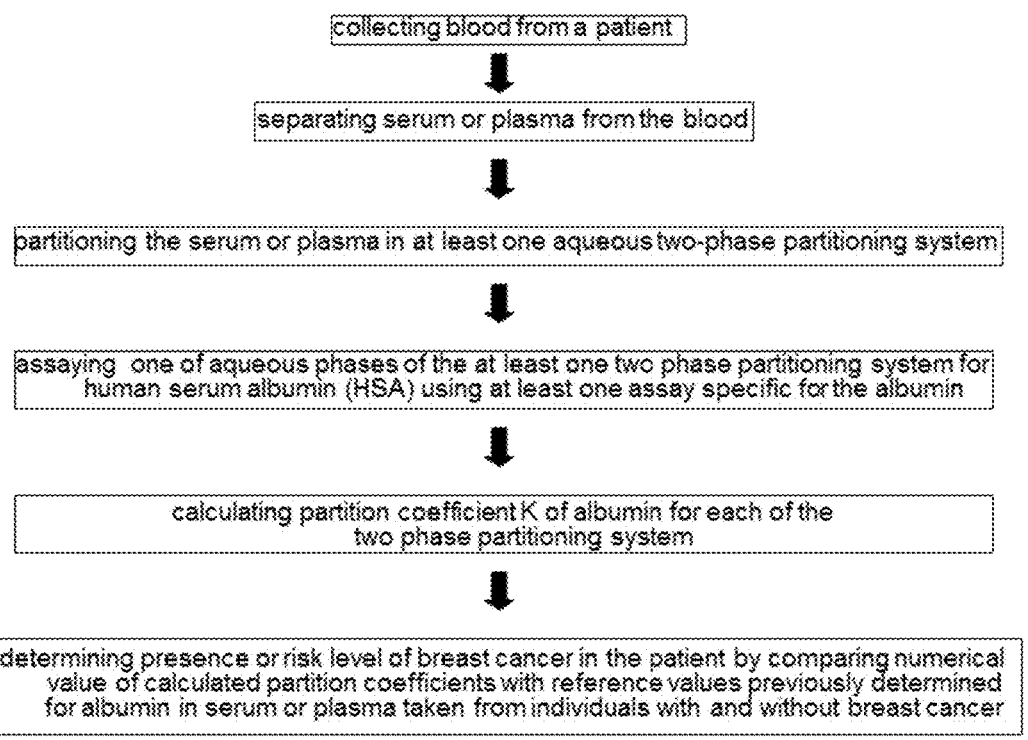
FIG. 4 shows a method associated with another embodiment of the invention.

Attention is turned to FIG. 4 which shows a flowchart in accordance with one embodiment of the instant invention. The flowchart shown in FIG. 4 includes the following: collecting blood from a patient; separating serum or plasma from the blood; partitioning the serum or plasma in at least one aqueous two-phase partitioning system; assaying one aqueous phase of the at least one two phase partitioning system for human serum albumin (HSA) using at least one assay specific for the albumin; calculating partition coefficient K of albumin for each aqueous phase of the two phase partitioning system based on the measured amount of HSA in the one aqueous phase; and, determining presence or risk level of breast cancer in the patient by comparing numerical value of calculated partition coefficients with reference values previously determined for albumin in serum or plasma taken from individuals with and without breast cancer, or from the same patient at different time. As previously discussed, breast cancer is shown here as a non-limiting example; in other embodiments, other cancers or disease states may be determined.

In one embodiment, determination of HSA concentration may be performed in only one phase of a two-phase aqueous system (e.g., only the upper phase or only the lower phase). In some cases, for instance, the total HSA concentration may be determined prior to partitioning; by knowing the amount present in one phase and the total amount originally present, then one can determine the amount of HSA in the remaining phase. Alternatively, one may omit measurement of HSA concentration in the sample, as HSA concentrations are generally known and one may use appropriate literature values for such determinations, or make reasonable approximations, e.g., based on the patient's age, sex, blood pressure, height, and/or weight, etc. Thus, only one phase for HSA concentration may be determined or measured. K may be calculated based on the one measured HSA concentration value and the other calculated HSA concentration value; the K value may be compared to known values for cancerous and non-cancerous states (or other disease states such as those described herein). In some cases, a medical determination may be performed based on the determined K value.

In some embodiments, HSA is partitioned between aqueous phases in a predetermined biphasic (or higher) liquid system. HSA enters both phases, but in general not at equal levels due to differences in the aqueous solvent characteristics in the two phases, e.g., as previously discussed. The specific amount entering a phase may in some cases be further related to HSA having at least one associated ligand. Additionally, the HSA dissolved in each phase varies between healthy (including benign) patients and those with diseases, e.g., cancers such as breast cancer. The aqueous-based liquids used in the partitioning system may in some embodiments be pre-selected to provide this differentiation of HSA behavior as a function of presence or absence of breast cancer in a patient. Once the HSA has been partitioned, in steps that may involve, for example, vortexing, mixing, centrifugation or other manipulations, the HSA in one phase may be assayed using techniques known to those of ordinary skill in the art, e.g., immuno-specific assays like ELISA. Such assays alternatively may be directed towards a ligand or a plurality of ligands associated with the HSA. With quantification of HSA or its associated ligands, one may determine a ratio of the amount of HSA (or ligands) in each phase as described above. This ratio, K, may vary significantly between HSA taken from healthy patients and those either with an active disease or those with a high risk for the disease, e.g., of cancers such as breast cancers. K may be compared to data previously collected for known healthy and known ill patients, or compared with previously measured values for the same patient. The K value may be determined as falling within values for healthy patients or within values for those known to have breast or other cancers, or a high risk factor for such cancers, etc. Since the individual disease biology may differ for each individual, conventional statistical techniques known to those of ordinary skill in the art used in the study of diagnostics, such as Receiver-Operating Characteristics, may be used to define a cut-off point for K, depending on the desired levels of sensitivity and specificity.

The ligands associated with HSA which allow for the differentiation may never be known, in some cases. Moreover, since cancer is a heterogeneous disease on the molecular level, such methods, which focuses on differential solubility of the HSA carrier protein that potentially binds a myriad of disease-associated molecules, may be advantageous in comparison with the conventional approach of isolating a single "silver bullet" biomarker. For instance, the ligands binding to HSA may, in reality, be composed of a family of different ligands or biomarkers, and their aggregate effect on HSA may be determined, even if the effect of any single biomarker is not completely determined. In some embodiments, one may isolate said ligands for the purpose of assigning them as biomarkers for certain cancers, such as breast cancer. Methods for removing biomolecules from HSA and analyzing said biomolecules are those traditionally used in protein chemistry work, and include chromatography, mass spectrometry, etc. Since one does not have to initially identify and define biomarkers in this embodiment, a great deal of effort may be saved instead by analyzing changes in HSA partitioning behavior as a function of the presence or absence of cancer, or the risk of cancer, according to certain embodiment of the invention.

Figure 5:
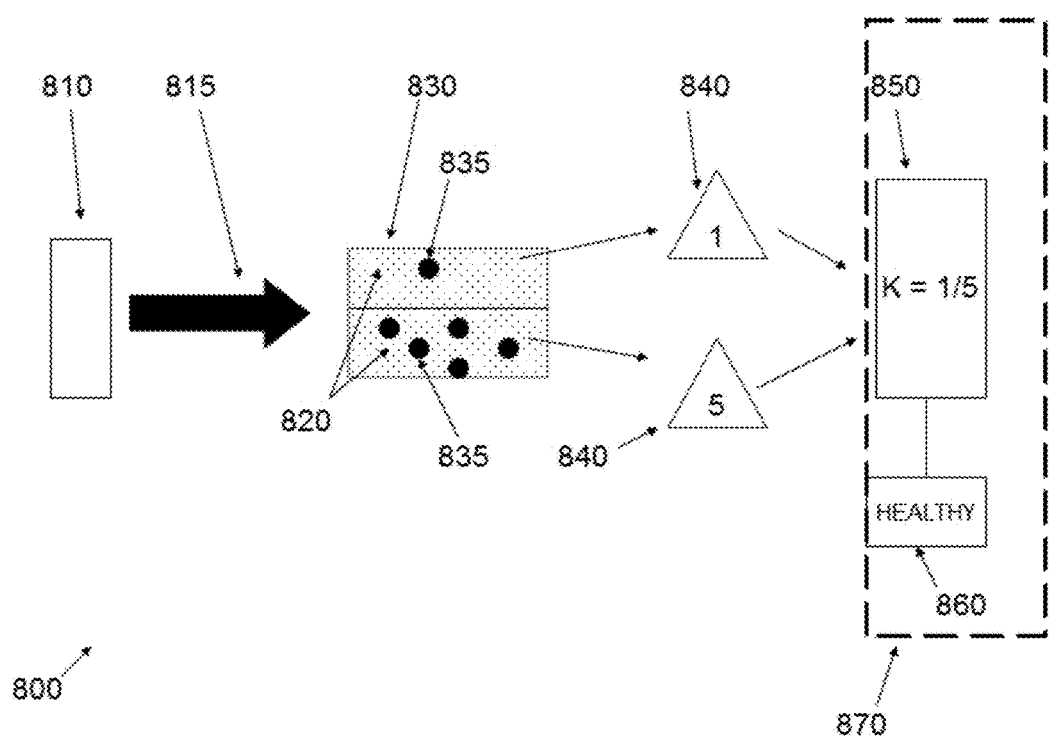
FIG. 5 shows a schematic view of one embodiment of the invention.

Attention is turned to FIG. 5 which shows yet another embodiment. In the example of FIG. 5, the components of a device associated with the breast cancer detection system 800 include: a unit for collecting blood 810 from a patient and separating 815 serum or plasma from the blood; at least one aqueous two-phase partitioning system 820; a co-current or counter-current chromatographic channel for partitioning 830 a portion of the serum or plasma in the two phase partitioning system; an assay 840 for determining the presence of human serum albumin 835 in aqueous phases of the two phase partitioning system; a computing element 850 adapted to determine a coefficient K, wherein K represents the distribution of human serum albumin 835 in the aqueous portions of the two-phase partitioning system; and, a determination element 860 adapted to compare the coefficient K with known values of K for blood samples of healthy individuals and individuals with cancers, such as breast cancer. It should be understood that all of the elements described in this embodiment may be included in a single unit or a small number of modular components; the elements are shown individually in this figure so as to aid in the understanding of the present invention.

The aqueous partition system 820 may be added to the chromatographic unit either before or with the serum sample including HSA. The serum sample may be introduced into the channel independently or together with one of the flowing phases, and HSA partitions between the phases as it travels downstream. When the equilibrium amounts of HSA are established between the phases, samples from one or both of the two phases are obtained, and the amounts of HSA in each phase are assayed using conventional techniques, and are used to calculate the partition coefficient, K, as described before. Such devices may employ microfluidics elements, and could one way to provide point-of-care capabilities for the present invention.

Computing element 850 and determination element 860 may generally be associated with a computing device 870 that may including a controller element (not shown) that directs all necessary tasks from the receipt of blood to producing a final determination of breast cancer presence. Computing device 370 may be realized as any relevant device and includes but is not limited to computers, handheld computers, tablet computers, cellular phones, laptop computers, and tabletop computers, or other computing devices known to those of ordinary skill in the art.

As mentioned, a variety of cancers may be determined in a blood sample (or other suitable fluid sample), e.g., by determining partitioning of HSA in an aqueous two-phase partitioning system. Examples of cancers include, but are not limited to: breast, prostate, lung, ovarian, colorectal, and brain cancer. Other non-limiting examples of cancers include biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Still other examples of cancers include lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia and heavy chain.

As discussed, HSA may be partitioned using an aqueous two-phase partitioning system or an aqueous multi-phase partitioning system, in certain embodiments. Aqueous two-phase systems may arise in aqueous mixtures of different water-soluble polymers or a single polymer and a specific salt. When two certain polymers, e.g., dextran (Dex) and polyethylene glycol (PEG), or a single certain polymer and a certain inorganic salt, e.g. polyvinylpyrrolidone (PVP) and sodium sulfate, are mixed in water above certain concentrations, the mixture separates into two immiscible aqueous phases. There is a discrete interfacial boundary separating two phases, one rich in one polymer and the other rich in the other polymer or inorganic salt. The aqueous solvent in both phases provides media suitable for biological products. Two-phase systems can be generalized to multiple phase system by using different chemical components, and aqueous systems with a dozen or more phases have been mentioned in the literature.

When a solute is introduced into such a two-phase system, it distributes between the two phases. Partitioning of a solute is characterized by the partition coefficient K defined as the ratio between the concentrations of the solute in the two immiscible phases at equilibrium. It was previously shown that phase separation in aqueous polymer systems results from different effects of two polymers (or a single polymer and a salt) on the water structure. As the result of the different effects on water structure, the solvent features of aqueous media in the coexisting phases differ from one another. The difference between phases can be demonstrated by dielectric, solvatochromic, potentiometric, and partition measurements.

The basic rules of solute partitioning in aqueous two-phase systems were shown to be similar to those in water-organic solvent systems. However, what differences do exist in the properties of the two phases in aqueous polymer systems are very small relative to those observed in water-organic solvent systems, as should be expected for a pair of solvents of the same (aqueous) nature. Importantly, the small differences between the solvent features of the phases in aqueous two-phase or multi-phase systems can be modified so as to amplify the observed partitioning that results when certain structural features are present, e.g., such as ligands on HSA.

It is known that the polymer and salt compositions of each of the phases depend upon the total polymer and salt composition of an aqueous two-phase system. The polymer and salt composition of a given phase, in turn, governs the solvent features of an aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media govern the sensitivity of a given aqueous two-phase system toward a particular type of solvent accessible chemical groups in the receptor. This sensitivity, type, and topography of the solvent accessible groups in two different proteins, for example, determine the possibility of separating or partitioning proteins such as HSA in a given aqueous two-phase system. One example of aqueous two-phase partitioning is described in U.S. Pat. No. 6,136,960, hereby incorporated in its entirety.

Without wishing to be bound by any theory, it is believed that partitioning of a biopolymer in aqueous two-phase systems depends on its three-dimensional structure and type and topography of chemical groups exposed to the solvent. Changes in the 3-D structure of a receptor induced by some effect, e.g., by binding of a ligand binding or by structural degradation, also change the topography of solvent accessible chemical groups in the biomolecule or both the topography and the type of the groups accessible to solvent. One result of these changes is an alteration in the partition behavior of the biomolecule or the ligand-bound-receptor. As a result, by monitoring the partition coefficient of an analyte, it is possible to detect a change in the state of a structure for which a partition coefficient is already known.

Similarly, such changes may be detected using other methods which have an underlying dependence upon the topography and/or the types of solvent accessible groups. Examples of such other methods include, but are not limited to, column liquid-liquid partition chromatography (LLCP), heterogeneous two-phase systems or a multiphase heterogeneous system.

In cases where a method as in determining a coefficient which reflects a relative partitioning, e.g., as in a partition coefficient, a single descriptor is obtained. While the many different aqueous two-phase systems all differ in their sensitivity toward various chemical groups, e.g., charged and non-polar groups, the presence of a detectable difference between two conformational states, in the form of a change in a partition coefficient, may result from a great many different mechanisms. As such, a similar change in a single partition coefficient may reflect very dissimilar conformational changes. In addition, in some cases, more than one partitioning coefficient may be obtained, e.g., as in a signature. See, e.g., U.S. Pat. No. 7,968,350, incorporated by reference in its entirety.

As used herein, "signature" refers to a particular representation of desired information, which can be defined as a set of relative measures of interaction described above obtained from experiments with different interacting components. Typically, a signature is used in place of more detailed information when the latter is difficult to obtain, or when it is not necessary to completely describe such information in order to make use of it. For example, fingerprinting individual people is a well-recognized technique to uniquely identify an individual (to a reasonable certainty), providing a conveniently obtained and conveniently dense information set instead of describing the individual using other representations, e.g., genetic makeup, or by using exhaustively physical description and other information.

An "interaction signature," a used herein, means a signature characteristic of interaction of a species with at least one other species, optionally also characteristic of interaction of either or both species with another species or an environment (medium) in which the species exist and/or with which the species interact. For example, an interaction signature may characterize interaction of a species with one phase of a multi-phase system, and with another phase of the multi-phase system, with an overall interaction signature characteristic of the relative interaction of the species with the two (or more) phases. As further examples, an interaction signature can be characteristic of interaction of a species with any number of phases of a multi-phase system, and interaction signatures can exist for interaction between and among a variety of species and a variety of phases of a multi-phase system.

In accordance with the desired attributes of a signature, an information set could be described by numbers, mathematical expressions, by visual representations or by other means that are known to those of skill in the art. The particular choice of how a signature is represented will primarily dependent upon the specific technique that is used to obtain the surrogate information that is used to construct the signature and on the manner in which the signature is ultimately going to be used. As will be recognized by those of skill in the art, many techniques have been developed to condense and convey information in a manner that would be suitable for use in establishing a signature or set of signatures.

Mathematical techniques suitable for obtaining a useful signature are numerous. They include, but are not limited to, linear or nonlinear mapping (e.g., artificial neural networks and partial least squares regression), matrix rotation and projection (e.g., principal component analysis and singular value decomposition), direct modeling using differential equations that reflect the underlying physical process, if the underlying physical process is known. Sometimes visual representations form superior signatures, especially if they readily convey the desired information, e.g., differences amongst individual sets, using shapes and colors which are easily conveyed to the observer.

Information sets to be used in generating signatures can comprise data from two or more trial or experimental conditions, e.g., two or more partition coefficients. In preferred embodiments, the method will use greater than 2, 3, 4, 5, 6, 8, 10 or 20 different sets of conditions. As will be recognized, the actual measurement or technique used to obtain a measurement is not limited to a specific technique. As described herein by way of example, the data can include partition coefficients. Other types of data and the means for obtaining the data therefor will also be recognized by those of skill in the art.

As mentioned, aqueous two-phase partitioning can be used to gather information for generating a signature. Aqueous two-phase partitioning described in U.S. Pat. No. 6,136,960, hereby incorporated in its entirety, is one method by which information can be obtained for generating a signature. Partitioning of a biopolymer in aqueous two-phase systems depends on its three-dimensional structure and type and topography of chemical groups exposed to the solvent. Changes in the 3-D structure of a receptor induced by some effect, e.g., by binding of a ligand binding or by structural degradation, also change the topography of solvent accessible chemical groups in the biomolecule or both the topography and the type of the groups accessible to solvent. One result of these changes is an alteration in the partition behavior of the biomolecule or the ligand-bound-receptor. As a result, by monitoring the partition coefficient of an analyte such as HSA, it is possible to detect a change in the state of a structure for which a partition coefficient is already known.

"Aqueous," as used herein, refers to the characteristic properties of a solvent/solute system wherein the solvating substance has a predominantly hydrophilic character. Examples of aqueous solvent/solute systems include those where water, or compositions containing water, is the predominant solvent.

"Aqueous multi-phase system," as used herein, refers to an aqueous system which consists of greater than one aqueous phase in which an analyte species can reside, and which can be used to characterize the structural state of the analyte species according to the methods described herein. For example, this includes aqueous system which can separate at equilibrium into two, three, or more immiscible phases. Aqueous multi-phase systems are known in the art and this phrase, as used herein, is not meant to be inconsistent with accepted meaning in the art.

An "interacting component" means a component, such as a phase of an aqueous multi-phase system, that can interact with a species and provide information about that species (for example, an affinity for the species). Multiple interacting components, exposed to a species, can define a system that can provide a "relative measure of interaction" between each component and the species. An interacting component can be aqueous or non-aqueous, can be polymeric, organic (e.g. a protein, small molecule, etc.), inorganic (e.g. a salt), or the like, or any combination. A set of interacting components can form a system useful in and in part defining any experimental method which is used to characterize the structural state of a species such as an analyte species according to the methods described herein. Typically, a system of interacting components can measure the relative interaction between the species and at least two interacting components. An aqueous multi-phase system is a species of a system of interacting components, and it is to be understood that where "Aqueous system" or "Aqueous multi-phase system" is used herein, this is by way of example only, and any suitable system of interacting components can be used.

Both aqueous two-phase and aqueous multi-phase systems, as used herein, also refer to systems analogous to those comprising only aqueous solutions or suspensions. For example, an aqueous two-phase system can include non-aqueous components in one or more phases that are not liquid in character. In this aspect, aqueous phase systems also refers to related techniques that rely on differential affinity of the biomolecule to one media versus another, wherein the transport of the biomolecule between one medium and, optionally, another medium occurs in an aqueous environment. Examples of such "heterogeneous phase systems" include, but are not limited to, HPLC columns or systems for liquid-liquid partition chromatography as are known to those of skill in the art.

"Partition coefficient," as used herein, refers to the coefficient which is defined by the ratio between the concentrations of the solute in the two immiscible phases at equilibrium. For example, the partition coefficient (K) of an analyte in a two-phase system is defined as the ratio of the concentration of analyte in the first phase to that in the second phase. For multi-phase systems, there are multiple partition coefficients wherein each partition coefficient defines the ratio of analyte in first selected phase and a second selected phase. It will be recognized that the total number of partition coefficients in any multi-phase system will be equal to the total number of phases minus one.

"Bind," as used herein, means the well understood receptor/ligand binding as well as other nonrandom association between an a biomolecule and its binding partner. "Specifically bind," as used herein describes a binding partner or other ligand that does not cross react substantially with any biomolecule other than the biomolecule or biomolecules specified.

Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Biomolecule," as used herein, means; peptides, polypeptides, proteins, protein complexes, nucleotides, oligonucleotides, polynucleotides, nucleic acid complexes, saccharides, oligosaccharides, carbohydrates, lipids and combinations, derivatives and mimetics thereof.

"Detectable," as used herein, refers the ability of a species and/or a property of the species to be discerned. One method of rendering a species detectable is to provide further species, that bind or interact with the first species, that comprise a detectable label. Examples of detectable labels include, but are not limited to, nucleic acid labels, chemically reactive labels, fluorescence labels, enzymic labels and radioactive labels.

Aqueous two-phase systems arise in aqueous mixtures of different water-soluble polymers or a single polymer and specific salts. For example, dextran and polyethylene glycol ("PEG") are mixed in water above certain concentrations, the mixture separates into two immiscible aqueous phases separated by a clear interfacial boundary. These two separated phases are said to have resolved. In one phase, the solution is rich in one polymer and, on the other side of this boundary in a second phase, the solution is rich in the other polymer. The aqueous solvent in both phases provides media suitable for biological products such as proteins or for other biomolecules.

Selection and modification of the types, as reflected in, for example, the chemical nature, structure, and molecular weight, of the phase-forming polymers and the concentration of the polymers can be used to vary the properties of the phases. In addition, the composition of the phases can also be changed by the addition of inorganic salts and/or organic additives. Changes to the composition of the phases can alter the properties of the phases. Examples of types of aqueous two-phase systems that are useful for detecting and/or characterizing the binding of a binding partner to a receptor include, but are not limited to, dextran/PEG, dextran/polyvinylpyrrolidone, PEG/salt, and polyvinylpyrrolidone/salt.

Biomolecules such as proteins, nucleic acids or other also distribute between the two phases when placed into such a system. This partitioning of a biomolecule between the two phases is fairly simple. In some respects, it is similar to extraction as is normally in the chemical arts. For example, in the case where phase-forming polymers are used, solutions comprising one or more of the two polymers and the biomolecule are mixed together such that both phase-forming polymers and the biomolecule are mixed. The resulting solution is resolved and the two-phase system is formed. Optionally, centrifugation can be used to enhance separation of the phases. It will be recognized by those of skill in the art that partitioning behavior of a biomolecule may be influenced by many variables, such as the pH, the polymers used, the salts used, other factors relating to the composition of the system, as well as other factors such as temperature, volume, etc. Optimization of these factors for desired effects can be accomplished by routine practice by those of skill in the relevant arts in combination with the current disclosure.

Evaluation of data from partitioning of a biomolecule can involve use of the partition coefficient ("K"), which is defined as the ratio between the concentrations of the biomolecule in the two immiscible phases at equilibrium. For example, the partition coefficient, K, of a protein is defined as the ratio of the protein in first phase to that in the second phase in a biphasic system. When multiple phase systems are formed, there can be multiple independent partition coefficients that could be defined between any two phases. From mass balance considerations, the number of independent partition coefficients will be one less than the number of phases in the system.

It will be recognized that the partition coefficient K for a given biomolecule of a given conformation will be a constant if the conditions and the composition of the two-phase system to which it is subjected remain constant. Thus, if there are changes in the observed partition coefficient K for the protein upon addition of a potential binding partner, these changes can be presumed to result from changes in the protein structure caused by formation of a protein-binding partner complex. "K", as used herein, is used as specifically mathematically defined herein, and in all instances also includes, by definition, any coefficient representing the relative measure of interaction between a species and at least two interacting components.

In order to determine the partition coefficient K of a protein or a mixture of a protein with another compound to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, and the protein mixture can be mixed in the amounts and conditions (e.g., pH from about 3.0 to about 9.0, temperature from about 4° C. to 60° C., salt concentration from 0.001 to 5 mole/kg) appropriate to bring the system to the desired composition and vigorously shaken. The system can then be allowed to equilibrate (resolve the phases). Equilibration can be accomplished by allowing the solution to remain undisturbed, or it can be accelerated by centrifugation, e.g., for 2-30 minutes at about 1000 to 4000 g or higher. Aliquots of each settled (resolved) phase can be withdrawn from both the upper and lower phases. The concentration of biomolecule can be determined for both the upper and lower phases.

Different assay methods may be used to determine the concentration of the biomolecules in each phase. The assays will depend upon the identity and type of biomolecule present. Examples of suitable assay techniques include, but are not limited to, spectroscopic, immunochemical, chemical, fluorescent, radiological and enzymatic assays. When the biomolecule is a peptide or protein, e.g., HSA, the common peptide or protein detection techniques can be used. These include direct spectrophotometry (monitoring the absorbance at 280 nanometers) and dye binding reactions with Coomassie Blue G-250 or fluorescamine, o-phthaldialdehyde, or other dyes and/or reagents. Alternatively, if the protein is either an antibody or an antigen, immunochemical assays can also be used.

The concentration of the biomolecule(s) in each phase can then be used to determine the partition coefficient, K, of the sample under the particular system conditions. Since K reflects only the ratio of the two concentrations, the absolute values are not typically required. It will be recognized that this can allow certain analytical procedures to be simplified, e.g., calibration can be eliminated in some instances.

The partition coefficient can then be compared with other K values. For example, a K value for a species can be compared to the K values for the species under different conditions, a K value for a species can be compared to the K values for the species when combined with other species, or a set of K values for a species can be compared to other sets of K values.

Additionally, if the biomolecule concentration in the two-phase system of a fixed composition is kept constant, the changes in the partition coefficient can be measured not as changes in the partition coefficient value, but as those in the biomolecule concentration in a given phase, for example, top phase of the system. This may be more efficient than the determination of the partition coefficient value from measurements of the biomolecule concentrations in each phase of a system.

Although the above has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. For example, certain embodiments of the present invention could be employed for general population screening and one could use HSA as a general carrier unit for detection of biomolecules not necessarily present in the blood: one could add exogenous samples to HSA solutions and then partition the HSA as described above, with the goal to detect a predetermined biomolecule.

The following documents are incorporated herein by reference in their entireties: U.S. Pat. Nos. 8,099,242; 6,136,960; and 8,041,513.

The following examples are intended to illustrate certain embodiments of the present invention, but do not exemplify the full scope of the invention.

EXAMPLE 1

In this example it is shown that albumin in human serum displays different partitioning behavior when present in blood serum from a group of patients with malignant breast tumor and a group of patients comprised of benign breast tumor and female healthy donors. This example further demonstrates that different partitioning systems may exhibit different levels of clinical specificity and degree of clinical differentiation power.

Human serum samples corresponding to malignant and benign or healthy clinical phenotypes were purchased from SeraCare Life Sciences. The diagnostic status of each sample was additionally provided by SeraCare Life Sciences. Sample aliquots were obtained frozen and stored at −80° C., and thawed and diluted 3-fold with water before introducing to the aqueous two phase systems.

Aqueous two-phase system was prepared with Ficoll®-70 (molecular weight of about 70,000), Dex-70 (molecular weight of about 70,000), and 0.10 M sodium phosphate buffer, pH 7.4. Ficoll is a commercially-available branched, high-mass, hydrophilic polysaccharide. The system in each tube was prepared by mixing the appropriate amounts of stock polymer and buffer solutions dispensed by a liquid handling workstation Hamilton ML-4000 into a microtube of a total volume of 1.2 mL up to a total volume of a mixture of 393 microliters. A varied amount (15, 30, 45, 60, and 75 microliters) of each serum sample and the corresponding amount (92, 77, 62, 47, and 32 microliters) of water were added to a system. The ratio between the volumes of the two phases of each system of a final volume of 500 microliters was as 1:1. The system was vigorously shaken and centrifuged for 60 min at 3500 g in a refrigerated centrifuge with a microplate rotor with the temperature maintained at 23° C. to speed the phase settling. Microtubes were taken out of the centrifuge, and aliquots of 50 microliters from the top and the bottom phases were withdrawn in duplicates and each diluted and mixed with appropriate reagents as indicated below, and used for further analysis.

A second aqueous two-phase system was prepared with Ficoll®-70 (molecular weight of about 70,000), Dex-70 (molecular weight of about 70,000), and 0.15 M NaSCN, 0.15 M $Na_2SO_4$, and 0.01 M sodium phosphate buffer, pH 7.4. The system in each tube was prepared by mixing the appropriate amounts of stock polymer, salt, and buffer solutions dispensed by liquid handling workstation Hamilton ML-4000 into a microtube of a total volume of 1.2 mL up to a total volume of a mixture of 419 microliters. A varied amount (15, 30, 45, 60, and 75 microliters) of each serum sample and the corresponding amount (70, 55, 40, 25, and 10 microliters) of water were added to a system. The ratio between the volumes of the two phases of each system of a final volume of 504 microliters was as 1:1. The system was vigorously shaken and centrifuged for 60 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted and mixed with appropriate reagents as indicated below and used for further analysis.

A third aqueous two-phase system was prepared with PEG-600 (polyethylene glycol with molecular weight of about 600), $Na_2SO_4$, and sodium/potassium phosphate buffer, pH 7.4. The system in each tube was prepared by mixing the appropriate amounts of stock polymer, salt, and buffer solutions dispensed by liquid handling workstation Hamilton ML-4000 into a microtube of a total volume of 1.2 mL up to a total volume of a mixture of 336 microliters. A varied amount (15, 30, 45, 60, and 75 microliters) of each serum sample and the corresponding amount (149, 134, 119, 104, and 89 microliters) of water were added to a system. The ratio between the volumes of the two phases of each system of a final volume of 500 microliters was as 1:1. The system was vigorously shaken and centrifuged for 30 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted and mixed with appropriate reagents as indicated below and used for further analysis.

A fourth aqueous two-phase system was prepared with PEG-600 (polyethylene glycol with molecular weight of about 600), $Na_2SO_4$, 0.15M NaCl, and sodium/potassium phosphate buffer, pH 7.4. The system in each tube was prepared by mixing the appropriate amounts of stock polymer, salt, and buffer solutions dispensed by liquid handling workstation Hamilton ML-4000 into a microtube of a total volume of 1.2 mL up to a total volume of a mixture of 375 microliters. A varied amount (15, 30, 45, 60, and 75 microliters) of each serum sample and the corresponding amount (110, 95, 80, 65, and 50 microliters) of water were added to a system. The ratio between the volumes of the two phases of each system of a final volume of 500 microliters was as 1:1. The system was vigorously shaken and centrifuged for 30 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted and mixed with appropriate reagents as indicated below and used for further analysis.

Immunoassay analysis was conducted using aliquots (each of 40 microliters volume) from the top and the bottom phases, diluted 10-fold with 0.9 wt. % NaCl solution in water. The diluted aliquots were mixed by shaking and 200 microliters from each diluted aliquot was transferred to sample cups of a clinical chemistry analyzer (Roche-Hitachi, model 902). A turbidity-based microalbumin immunoassay was performed according to the manufacturer's (Roche) protocol, and the albumin concentration in each aliquot was recorded. The measured albumin concentration values in diluted aliquots from the top phases were plotted as a function of the albumin concentration values of the similarly diluted aliquots from the bottom phases. The partition coefficient for albumin was determined as a slope of the plotted linear curve. While the partition coefficient is defined as the ratio of the top to bottom phase concentrations, performing the series dilution experiments as described herein and using the slope of the linear regression line defines the partition coefficient value K to a greater accuracy, although the two definitions are equivalent.

The partition coefficients for albumin are presented in Table 1 (below). The data presented in Table 1 demonstrate that HSA partitioned in aqueous partitioning systems could be used to classify clinical samples according to their phenotype source as cancer or other (benign or normal). It was also demonstrated that aqueous partitioning systems of different chemical compositions could be devised, and would provide different degrees of capability for said classification ability. The final selection of an optimal system could be done using a sufficiently statistically powered group of samples of cancer and benign/normal origins, as defined using acceptable gold-standard diagnostics techniques.

TABLE 1

Partition coefficients for albumin in serum samples from patients with diagnostic status as indicated in different aqueous two-phase systems.

| Partitioning System | Partition coefficient K for albumin in serum from patients with | | | |
| --- | --- | --- | --- | --- |
| | Benign breast tumor or no tumor | | Malignant breast tumor | |
| Dextran-Ficoll ®-NaPB | 2.18 | 0.03 | 2.15 | 0.02 |
| | 2.19 | 0.03 | | |
| Dex-Ficoll ®-NaSCN—$Na_2SO_4$—NaPB | 0.330 | 0.009 | 0.29 | 0.011 |
| | 0.342 | 0.005 | 0.29 | 0.010 |
| PEG-600- $Na_2SO_4$—KNaPB | 2.13 | 0.02 | 2.39 | 0.036 |
| | 2.19 | 0.02 | 2.25 | 0.041 |
| PEG-600- $Na_2SO_4$—NaCl—KnaPB | 1.26 | 0.01 | 1.116 | 0.003 |
| | 1.29 | 0.02 | 1.02 | 0.098 |

EXAMPLE 2

In this example it was demonstrated that the partition coefficients of albumin in human serum from a group of patients with early (stage I) breast cancer are significantly different from the partition coefficients of albumin in human serum from a second group of patients with benign breast tumors.

Human serum samples corresponding to malignant and benign or healthy clinical phenotypes were purchased from Proteogenix, Inc. The diagnostic status of each sample was also provided by Proteogenix, Inc. Samples aliquots were obtained frozen and stored at −80° C., and thawed and diluted 3-fold with water before introducing to the aqueous two phase systems.

Aqueous two-phase system was prepared with PEG-1000 (polyethylene glycol with molecular weight of about 1,000), Ficoll®-70 (molecular weight of about 70,000), NaCl, and potassium citrate buffer, pH 6.8. The system in each tube was prepared by mixing the appropriate amounts of stock polymer and buffer solutions dispensed by a liquid handling workstation Hamilton ML-4000 into a microtube of a total volume of 1.2 mL up to a total volume of a mixture of 420 microliters. A varied amount (20, 30, 40, 50, 60, and 70 microliters) of each serum sample and the corresponding amount (60, 50, 40, 30, 20, and 10 microliters) of water were added to a system. The ratio between the volumes of the two phases of each system of a final volume of 500 microliters was as 1:1. The system was vigorously shaken and centrifuged for 60 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted and mixed with appropriate reagents as indicated below and used for further analysis.

Immunoassay analysis was conducted with aliquots (each of 40 microliters volume) from the top and the bottom phases, diluted 10-fold with 0.9 wt. % NaCl solution in water. The diluted aliquots were mixed by shaking and 200 microliters from each diluted aliquot was transferred to the sample cups of clinical chemistry analyzer (Roche-Hitachi, model 902). The turbidity-based microalbumin immunoassay was performed according to the manufacturer's (Roche) protocol, and the albumin concentration in each aliquot was recorded. The measured albumin concentration values in diluted aliquots from the top phases were plotted as a function of the albumin concentration values of the similarly diluted aliquots from the bottom phases. The partition coefficient for albumin was determined as a slope of the linear curve.

Figure 6:
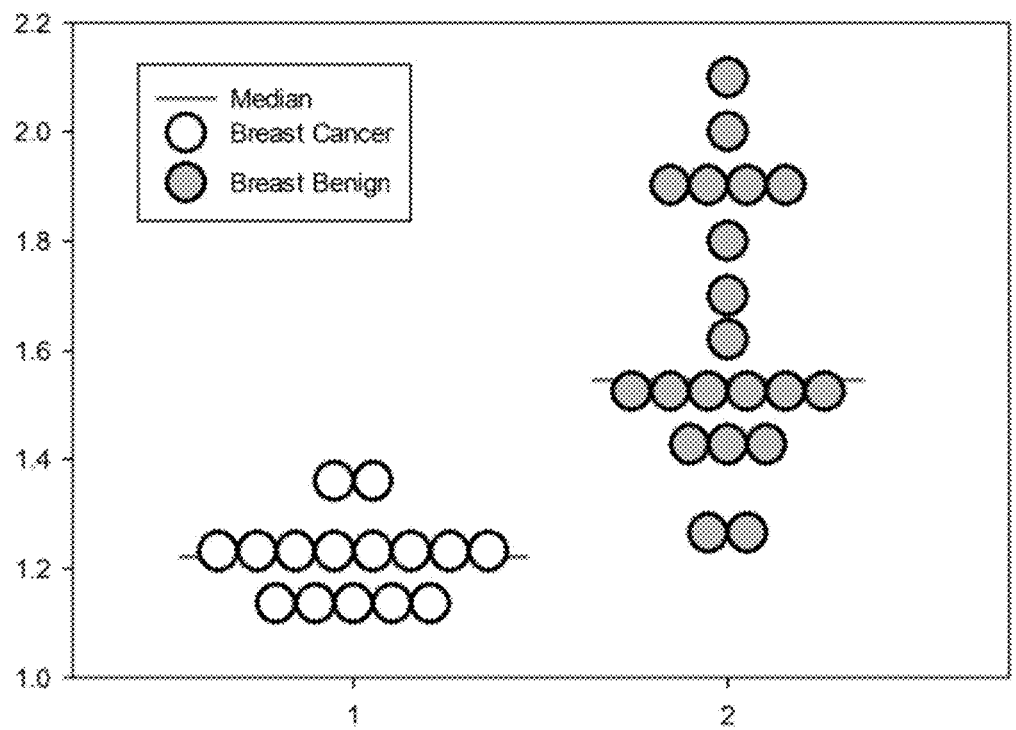
FIG. 6 shows a dot histogram corresponding to the data in Table 2 for early stage breast cancer and normal/benign groups, according to another embodiment of the invention.
Figure 7:
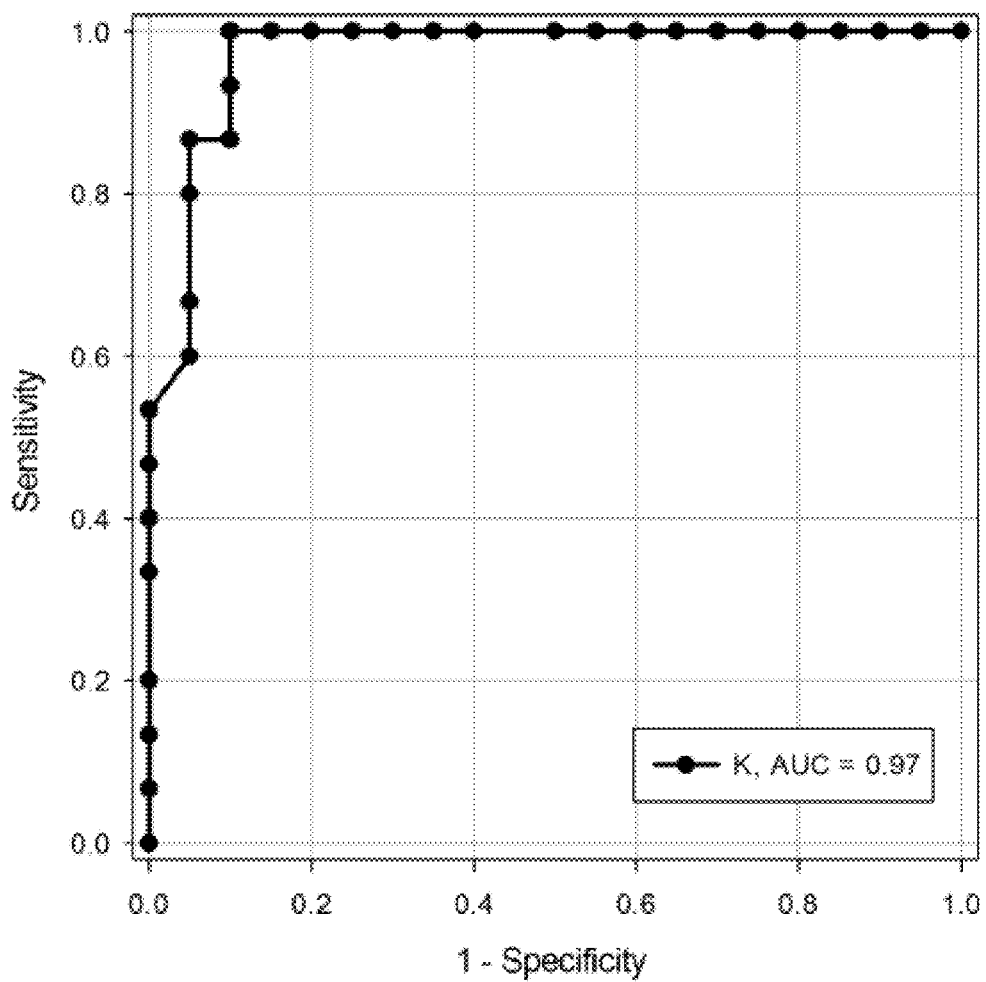
FIG. 7 shows a Receiver-Operating Characteristic plot of the data in Table 2, in one embodiment.

The partition coefficients for albumin in examined serum samples from patients with diagnostic status indicated are presented in Table 2 (below) and illustrated in the dot histogram of FIG. 6. The data presented in Table 2 demonstrate that there is a statistically significant difference between the median values of the partition coefficients of albumin in serum from patients with early (stage 1) breast cancer and those corresponding to albumin in serum from patients with benign breast tumor. Furthermore, while the separation between the two groups is not perfect, as in any diagnostics technology, it nevertheless clearly provides means to clinically distinguish between the two phenotypes with appropriate specificity and sensitivity levels selected for the desired clinical application. Additionally, the data in Table 2 also indicate also that confounding personal history is not related to the value of the partition coefficient. Finally, statistical techniques such as Receive-Operating Characteristics analysis could be performed (FIG. 7) and used to determine proper cut-off values of the K statistic. As an example, selecting K=1.39 provides for 100% sensitivity with 90% specificity for the test.

Human serum samples corresponding to malignant and benign or healthy clinical phenotypes were purchased from SeraCare Life Sciences. The diagnostic status of each sample was provided by SeraCare Life Sciences. Samples aliquots were obtained frozen and stored at −80° C., and thawed and diluted 3-fold with water before introducing to the aqueous two phase systems.

Aqueous two-phase system was prepared with PEG-1000 (polyethylene glycol with molecular weight of about 1,000), Ficoll®-70 (molecular weight of about 70,000), and potassium citrate buffer, pH 6.8. The system in each tube was prepared by mixing the appropriate amounts of stock polymer and buffer solutions dispensed by liquid handling workstation Hamilton ML-4000 into a microtube of a total volume of 1.2 mL up to a total volume of a mixture of 420 microliters. A varied amount (20, 30, 40, 50, 60, and 70 microliters) of each serum sample and the corresponding amount (60, 50, 40, 30, 20, and 10 microliters) of water were added to a system. The ratio between the volumes of the two phases of each system of a final volume of 500 microliters was as 1:1. The system was vigorously shaken and centrifuged for 60 min at 3500 g in a refrigerated centrifuge with a microplate rotor with the temperature maintained at 23° C.

TABLE 2

Partition coefficients for albumin in various serum samples from patients with diagnostic status as indicated in the aqueous two-phase system PEG-1000-Ficoll ®-70-NaCl-potassium citrate buffer, pH 6.8.

| Patients with early stage breast cancer | | | | | Patients with negative breast tumor biopsy | | | |
|---|---|---|---|---|---|---|---|---|
| Age | Pathology | Personal history | K-value | Error | Age | Personal history | K-value | Error |
| 34 | G3; T1N0M0 | chronic gastritis | 1.25 | 0.063 | 19 | no | 1.62 | 0.033 |
| 55 | G2; T1N0M0 | chronic cystitis | 1.16 | 0.077 | 55 | hypertension | 1.41 | 0.069 |
| 63 | G3; T1N0M0 | No | 1.24 | 0.053 | 28 | No | 1.70 | 0.085 |
| 63 | G1; T1N0M0 | ischemia; hypertension | 1.26 | 0.054 | 59 | ischemia; atherosclerosis | 1.89 | 0.052 |
| 67 | G3; T1N0M0 | Ischemia | 1.12 | 0.051 | 49 | Hypertension | 1.51 | 0.039 |
| 46 | G2; T1N0M0 | No | 1.25 | 0.065 | 21 | No | 1.30 | 0.084 |
| 83 | G2; T1N0M0 | ischemia; atherosclerosis | 1.21 | 0.057 | 38 | chronic bronchitis | 1.47 | 0.088 |
| 38 | G3; T1N0M0 | No | 1.16 | 0.023 | 55 | Hypertension | 1.88 | 0.042 |
| 84 | G2; T1N0M0 | ischemia; hypertension | 1.23 | 0.028 | 30 | no | 1.54 | 0.029 |
| 56 | G2; T1N0M0 | cholelithiasis | 1.22 | 0.070 | 73 | ischemia; atherosclerosis | 1.49 | 0.018 |
| 69 | G2; T1N0M0 | ischemia; atherosclerosis | 1.38 | 0.047 | 31 | No | 1.80 | 0.089 |
| 65 | G1; T1N0M0 | Ischemia | 1.19 | 0.087 | 27 | No | 2.0 | 0.11 |
| 66 | G2; T1N0M0 | Hypertension | 1.14 | 0.050 | 48 | bronchitis; chronic gastritis | 1.54 | 0.042 |
| 56 | G3; T1N0M0 | Hypertension | 1.34 | 0.029 | 47 | No | 1.23 | 0.046 |
| 60 | G3; T1N0M0 | ischemia; hypertension | 1.1 | 0.41 | 41 | No | 1.52 | 0.029 |
| | | | | | 49 | No | 1.40 | 0.075 |
| | | | | | 44 | No | 2.1 | 0.12 |
| | | | | | 32 | No | 1.55 | 0.078 |
| | | | | | 58 | No | 1.9 | 0.16 |
| | | | | | 39 | No | 1.94 | 0.096 |

EXAMPLE 3

In this example it was demonstrated that the partition coefficients of albumin in human serum from different patients with early (stage I) breast cancer are significantly different from the partition coefficients of albumin in human serum from different patients with benign breast tumor and patients with various malignant or benign tumors of different tissue origins, thus demonstrating potential tissue-selectivity of a test using the present invention.

to speed the phase settling. Microtubes were taken out of the centrifuge, and aliquots of 40 microliters from the top and the bottom phases were withdrawn in duplicates and each diluted and mixed with appropriate reagents as indicated below and used for further analysis performed.

Immunoassay analysis was conducted with aliquots (each of 40 microliters volume) from the top and the bottom phases were diluted 10-fold with 0.9 wt. % NaCl solution in water. The diluted aliquots were mixed by shaking and 200 microliters from each diluted aliquot was transferred to cups of clinical chemistry analyzer (Roche-Hitachi, model 902). The turbidity-based microalbumin immunoassay was performed according to the manufacturer's (Roche) protocol, and the albumin concentration in each aliquot was recorded. The measured albumin concentration values in diluted aliquots from the top phases were plotted as a function of the albumin concentration values of the similarly diluted aliquots from the bottom phases. The partition coefficient for albumin was determined as a slope of the linear curve.

The partition coefficients for albumin are presented in Table 3 (below). The means for each group of samples corresponding to the same disease phenotype are plotted in FIG. 8. The data demonstrate that it was possible to develop an appropriate chemical composition of aqueous partitioning system that could differentiate between breast cancer samples, and those corresponding to either benign or normal samples, or other benign or cancer samples of different types of cancers. Furthermore, this particular chemical composition was designed to validate a negative (benign) diagnosis made, e.g., by mammography. Such a differential diagnosis with patients presenting suspicious imaging results are often sent to invasive biopsies and/or other expensive procedures. Other chemical compositions of aqueous partitioning systems could be developed for, e.g., denote only cancerous condition of the breast with other cancers and benign conditions of the breast resulting in significantly different K values.

TABLE 3

Partition coefficients for albumin in various serum samples from patients with diagnostic status as indicated in the aqueous two-phase system PEG-1000-Ficoll ®-70-potassium citrate buffer, pH 6.8 (BC—breast cancer; BB—breast benign.

| Age | Pathology | K-value | Error +/− | Age | Pathology | K-value | Error +/− |
|---|---|---|---|---|---|---|---|
| 80 | BC; T1N0M0 | 3.07 | 0.04 | 68 | BB | 3.31 | 0.071 |
| 45 | BC, Stage 1 | 3.4 | 0.24 | 48 | BB | 4.8 | 0.27 |
| 68 | BC, Stage 1 | 3.09 | 0.06 | 42 | BB | 5.1 | 0.13 |
| 42 | BC, Stage 1 | 3.63 | 0.053 | 40 | BB | 4.0 | 0.2 |
| 78 | BC, Stage 1 | 3.13 | 0.046 | 26 | BB | 4.5 | 0.12 |
| 42 | BC, Stage 1 | 2.8 | 0.16 | 28 | BB | 4.08 | 0.075 |
| 91 | BC, Stage 1 | 3.36 | 0.044 | 35 | BB | 3.98 | 0.021 |
| n/a | BC, Stage 1 | 2.6 | 0.12 | 41 | BB | 4.6 | 0.3 |
| n/a | BC, Stage 1 | 2.92 | 0.034 | 31 | BB | 4.0 | 0.11 |
| n/a | BC, Stage 1 | 2.99 | 0.034 | 44 | BB | 4.26 | 0.021 |
| n/a | BC, Stage 1 | 3.37 | 0.071 | 56 | BB | 4.1 | 0.05 |
| n/a | BC, Stage 1 | 2.98 | 0.05 | 41 | BB | 3.24 | 0.075 |
| n/a | BC, Stage 1 | 3.18 | 0.046 | n/a | Healthy | 4.15 | 0.037 |
| 34 | BC; G3; T1N0M0 | 3.4 | 0.15 | n/a | Healthy | 4.07 | 0.074 |
| 55 | BC; G2; T1N0M0 | 3.62 | 0.051 | n/a | Healthy | 4.07 | 0.064 |
| 63 | BC; G3; T1N0M0 | 3.0 | 0.13 | 67 | Healthy | 4.07 | 0.095 |
| 63 | BC; G1; T1N0M0 | 3.1 | 0.04 | 52 | Healthy | 4.6 | 0.17 |
| 67 | BC; G3; T1N0M0 | 2.79 | 0.038 | 19 | BB | 4.5 | 0.2 |
| 46 | BC; G2; T1N0M0 | 2.59 | 0.075 | 55 | BB | 3.9 | 0.44 |
| 83 | BC; G1; T1N0M0 | 2.75 | 0.077 | 28 | BB | 4.4 | 0.25 |
| 73 | BC; G3; T1N0M0 | 3.6 | 0.14 | 59 | BB | 4.6 | 0.2 |
| 38 | BC; G3; T1N0M0 | 3.09 | 0.032 | 49 | BB | 5.1 | 0.21 |
| 84 | BC; G2; T1N0M0 | 3.51 | 0.098 | 21 | BB | 3.23 | 0.084 |
| 56 | BC; G2; T1N0M0 | 3.4 | 0.14 | 38 | BB | 2.9 | 0.14 |
| 69 | BC; G2; T1N0M0 | 3.33 | 0.088 | 55 | BB | 5.9 | 0.12 |
| 65 | BC; G1; T1N0M0 | 3.5 | 0.15 | 30 | BB | 3.9 | 0.14 |
| 66 | BC; G2; T1N0M0 | 3.40 | 0.082 | 73 | BB | 3.9 | 0.12 |
| 60 | BC; G3; T1N0M0 | 3.10 | 0.071 | 31 | BB | 4.1 | 0.23 |
| 56 | BC; G3; T1N0M0 | 3.7 | 0.15 | 27 | BB | 3.9 | 0.12 |
| 55 | BC; G3; T1N0M0 | 3.4 | 0.17 | 48 | BB | 4.4 | 0.18 |
| 55 | BC; G2; T1N0M0 | 2.7 | 0.11 | 47 | BB | 2.42 | 0.042 |
| 64 | BC; G2; T1N0M0 | 2.48 | 0.025 | 41 | BB | 3.6 | 0.11 |
| 60 | BC; G2; T1N0M0 | 2.63 | 0.072 | 49 | BB | 2.56 | 0.072 |
| 47 | BC; G2; T1N0M0 | 2.99 | 0.085 | 44 | BB | 2.54 | 0.054 |
| 48 | BC; G2; T1N0M0 | 3.08 | 0.063 | 32 | BB | 5.7 | 0.23 |
| 46 | BC; G2; T1N0M0 | 3.1 | 0.2 | 50 | BB | 4.34 | 0.092 |
| 75 | BC; G2; T1N0M0 | 3.63 | 0.066 | 62 | BB | 3.72 | 0.061 |
|  |  |  |  | 48 | BB | 2.6 | 0.048 |

TABLE 3-continued

Partition coefficients for albumin in various serum samples from patients with diagnostic status as indicated in the aqueous two-phase system PEG-1000-Ficoll ®-70-potassium citrate buffer, pH 6.8 (BC—breast cancer; BB—breast benign.

| Age | Pathology | K-value | Error +/− | Age | Pathology | K-value | Error +/− |
|---|---|---|---|---|---|---|---|
| 62 | Colon Cancer | 4.2 | 0.25 | 50 | BB | 3.70 | 0.098 |
| 71 | Colon Cancer | 4.2 | 0.14 | 65 | BB | 3.6 | 0.11 |
| 78 | Colon Cancer | 4.4 | 0.2 | 58 | BB | 4.5 | 0.11 |
| 69 | Colon Cancer | 4 | 0.16 | 39 | BB | 4.5 | 0.15 |
| 73 | Colon Cancer | 4.1 | 0.22 |  |  |  |  |
| 85 | Colon Cancer | 4.2 | 0.69 | 42 | Lung Cancer | 4.5 | 0.18 |
|  |  |  |  | 57 | Lung Cancer | 4.3 | 0.27 |
| 68 | Colon Benign | 4.3 | 0.55 | 49 | Lung Cancer | 4.3 | 0.29 |
| 71 | Colon Benign | 6.0 | 0.61 | 64 | Lung Cancer | 4.4 | 0.8 |
| 75 | Colon Benign | 4.3 | 0.3 | 68 | Lung Cancer | 4.1 | 0.15 |
| 69 | Colon Benign | 4.8 | 0.23 |  |  |  |  |
| 74 | Colon Benign | 4.8 | 0.1 | 72 | Pancreatic cancer | 4.0 | 0.14 |
| 78 | Colon Benign | 4.1 | 0.23 | 74 | Pancreatic cancer | 4.4 | 0.14 |
|  |  |  |  | 69 | Pancreatic cancer | 4.0 | 0.2 |
| 72 | Prostate cancer | 4.13 | 0.075 | 81 | Pancreatic cancer | 3.97 | 0.094 |
| 69 | Prostate cancer | 4.9 | 0.17 |  |  |  |  |
| 81 | Prostate cancer | 4.7 | 0.47 |  |  |  |  |
| 88 | Prostate cancer | 4.32 | 0.085 |  |  |  |  |
| 74 | Prostate cancer | 4.14 | 0.035 |  |  |  |  |
| 68 | Prostate cancer | 4.4 | 0.38 |  |  |  |  |
| 71 | Prostate cancer | 4.8 | 0.3 |  |  |  |  |
| 87 | Prostate cancer | 5.2 | 0.33 |  |  |  |  |
| 69 | Prostate Benign | 5.9 | 0.45 |  |  |  |  |

EXAMPLE 4

In this example it is demonstrated that the present invention could also be used to differentiate physiological conditions other than cancer. In this example it is shown that the partition coefficients of albumin in human serum from different patients with nonalcoholic fatty liver disease (NAFLD) are significantly different from the partition coefficients of albumin in human serum from healthy donors.

Human serum samples were purchased from SeraCare Life Sciences and PromedDx, Inc. Samples were obtained frozen and were aliquoted and stored at −80° C. Diagnostic status of patients was provided by both vendors. Samples aliquots were thawed, brought to the room temperature, and diluted 3-fold with water before introducing to aqueous two phase systems.

The aqueous two-phase system prepared with PEG-1000 (polyethylene glycol with molecular weight of about 1,000), Ficoll®-70 (molecular weight of about 70,000), NaCl and potassium citrate buffer, pH 6.8. Each system was prepared by mixing the appropriate amounts of stock polymer and buffer solutions dispensed by liquid handling workstation Hamilton ML-4000 into a microtube of a total volume of 1.2 mL up to a total volume of a mixture of 440 microliters. A varied amount (10, 25, and 40 microliters) of each serum sample and the corresponding amount (30, 15, and 0 microliters) of water were added to a system. The ratio between the volumes of the two phases of each system of a final volume of 480 microliters was as 1:1. The system was vigorously shaken and centrifuged for 60 min at 3500 g in a refrigerated centrifuge with a microplate rotor with the temperature maintained at 23° C. to speed the phase settling.

Microtubes were taken out of the centrifuge, and aliquots of 40 microliters from the top and the bottom phases were withdrawn in duplicates and each diluted and mixed with appropriate reagents as indicated below and used for further analysis performed as described below.

The other aqueous two-phase system contained 19.2 wt. % PEG-1000 (polyethylene glycol with molecular weight of about 1,000), 5.8 wt. % Ficoll®-70 (molecular weight of about 70,000), 0.10 M $Na_2SO_4$. and 18.2 wt. % potassium citrate buffer, pH 6.8. Each system was prepared by mixing the appropriate amounts of stock polymer and buffer solutions dispensed by liquid handling workstation Hamilton ML-4000 into a microtube of a total volume of 1.2 mL up to a total volume of a mixture of 440 microliters. A varied amount (10, 25, and 40 microliters) of each serum sample and the corresponding amount (30, 15, and 0 microliters) of water were added to a system. The ratio between the volumes of the two phases of each system of a final volume of 480 microliters was as 1:1. The system was vigorously shaken and centrifuged for 60 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted and mixed with appropriate reagents as indicated below and used for further analysis performed as described below.

For immunoassay analysis aliquots (each of 40 microliters volume) from the top and the bottom phases were diluted 10-fold with 0.9 wt. % NaCl solution in water. The diluted aliquots were mixed by shaking and 200 microliters from each diluted aliquot was transferred to cups of clinical chemistry analyzer (Roche-Hitachi, model 902). The turbidity-based microalbumin immunoassay was performed according to the manufacturer (Roche) protocol, and the albumin concentration in each aliquot was registered. The measured albumin concentration values in diluted aliquots from the top phases were plotted as a function of the albumin concentration values of the similarly diluted aliquots from the bottom phases. The partition coefficient for albumin was determined as a slope of the linear curve representing the slope.

The partition coefficients for albumin in examined serum samples from patients with diagnostic status indicated are presented in Table 4. The data presented in Table 4 demonstrate that there is a significant difference between partition coefficients of albumin in serum from patients with NAFLD and partition coefficients of albumin in serum from healthy donors.

TABLE 4

Partition coefficients for albumin in serum samples from patients with diagnostic status indicated in aqueous two-phase system prepared with PEG-1000, Ficoll ®-70, potassium citrate buffer, pH 6.8 with different salts additives.

| Salt additive | Partition coefficient K for albumin in serum from patients with | | | |
| --- | --- | --- | --- | --- |
| | Healthy donors | | NAFLD | |
| $Na_2SO_4$ | 5.7 | 0.46 | 3.5 | 0.36 |
| | 5.5 | 0.32 | 3.6 | 0.52 |
| | | | 3.2 | 0.23 |
| M NaCl | 1.5 | 0.21 | 0.96 | 0.089 |
| | 1.4 | 0.32 | 0.93 | 0.060 |
| | | | 0.81 | 0.012 |

Unless otherwise defined, all technical and/or scientific terms used herein have the same meaning as commonly understood by one of ordinary skill in the art to which the invention pertains. Terms such as "biomolecule," "ligand," "cancer," breast cancer," "two-phase partitioning system," "ELISA," and other terms may have their normal meanings in the art, unless otherwise stated.

As used herein the term "about" refers to +/−10%.

The term "partitioning system" or "biphasic system" or alike refer to a liquid system, commonly with predominantly aqueous base and with a combination of soluble polymers of various molecular weights such as poly-ethylene-glycol, dextran, Ficoll®, etc., and other additives, including salts, surfactants, etc. A partitioning system may be prepared to physically result in phase separation, meaning that at least two distinct phases appear with markedly different solvent properties, such as relative hydrophobicity, ionic composition, etc.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

All technical terms may have their normal meaning as applied to the art unless otherwise specified.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of treating a subject comprising:
   partitioning a first sample arising from a subject in a first aqueous two-phase partitioning system, wherein the first sample is blood;
   measuring a first distribution of human serum albumin (HSA) within the phases of the first partitioning system and determining a first partition coefficient of the first partitioning system;
   partitioning a second sample in a second aqueous two-phase partitioning system, wherein the second aqueous two-phase partitioning system is substantially chemically identical to the first aqueous two-phase partitioning system, wherein the second sample is a control;
   measuring a second distribution of HSA within the phases of the second partitioning system, and determining the second partition coefficient of the second partition coefficient;
   identifying the presence of a ligand attached to HSA in the first sample based on a difference between the first distribution of HSA and the second distribution of HSA, as determined by the difference in the partition coefficients; and
   treating the subject with an anti-cancer drug based on the presence of the ligand attached to the HSA.

2. The method of claim 1, wherein the first sample is a serum sample.

3. The method of claim 1, wherein the first sample is a plasma sample.

4. The method of claim 1, wherein the ligand is a protein or a peptide.

5. The method of claim 1, wherein measuring the first distribution of HSA within the phases of the first partitioning system comprises determining a first amount of HSA within a first phase of the aqueous two-phase partitioning system, and determining a second amount of HSA within a second phase of the aqueous two-phase partitioning system.

6. The method of claim 5, wherein determining the first amount of HSA within a first phase of the aqueous two-phase partitioning system comprises determining the first amount of HSA within a first phase of the aqueous two-phase partitioning system using an enzyme-linked immunosorbent assay (ELISA).

7. The method of claim 5, wherein determining the first amount of HSA within a first phase of the aqueous two-phase partitioning system comprises determining the first amount of HSA within a first phase of the aqueous two-phase partitioning system using chromatography.

* * * * *